(12) United States Patent
Powell, Jr.

(10) Patent No.: US 10,414,812 B2
(45) Date of Patent: Sep. 17, 2019

(54) FULLY-HUMAN T-CELL RECEPTOR SPECIFIC FOR THE 369-377 EPITOPE DERIVED FROM THE HER2/NEU (ERBB2) RECEPTOR PROTEIN

(71) Applicant: THE TRUSTEES OF THE UNIVERSITY OF PENNSYLVANIA, Philadelphia, PA (US)

(72) Inventor: Daniel J. Powell, Jr., Bala Cynwyd, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 15/550,811

(22) PCT Filed: Feb. 11, 2016

(86) PCT No.: PCT/US2016/017521
§ 371 (c)(1),
(2) Date: Aug. 14, 2017

(87) PCT Pub. No.: WO2016/133779
PCT Pub. Date: Aug. 25, 2016

(65) Prior Publication Data
US 2018/0030110 A1 Feb. 1, 2018

Related U.S. Application Data

(60) Provisional application No. 62/116,864, filed on Feb. 16, 2015.

(51) Int. Cl.
| | |
|---|---|
| *A61K 39/00* | (2006.01) |
| *C12Q 1/6876* | (2018.01) |
| *C12N 15/86* | (2006.01) |
| *C07K 14/725* | (2006.01) |
| *C07K 14/82* | (2006.01) |
| *C07K 14/47* | (2006.01) |
| *C12N 9/12* | (2006.01) |
| *C07K 16/28* | (2006.01) |

(52) U.S. Cl.
CPC ...... *C07K 14/7051* (2013.01); *C07K 14/4705* (2013.01); *C07K 14/82* (2013.01); *C07K 16/28* (2013.01); *C12N 9/12* (2013.01)

(58) Field of Classification Search
None
See application file for complete search history.

(56) References Cited

U.S. PATENT DOCUMENTS

| | | | | |
|---|---|---|---|---|
| 2005/0066375 A1* | 3/2005 | Thiam | ............ | C07K 14/70517 800/8 |
| 2012/0128704 A1* | 5/2012 | Schendel | ........... | C07K 14/7051 424/185.1 |

FOREIGN PATENT DOCUMENTS

| | | | |
|---|---|---|---|
| WO | WO 97/32603 | * | 9/1997 |
| WO | 2010012829 A1 | | 2/2010 |
| WO | WO2010089412 | * | 8/2010 |
| WO | 2012038055 A1 | | 3/2012 |
| WO | 2014091034 A1 | | 6/2014 |

OTHER PUBLICATIONS

SCORE Search Results Details for Application 15550811 and Search Result 20180207_155823 us-15-550-811-3.rng. pp. 1-35; Mar. 30, 2018.*
Edwards et al The Remarkable Flexibility of the Human Antibody Repertoire; Isolation of Over One Thousand Different Antibodies to a Single Protein, BLyS J. Mol. Biol. (2003) 334, 103-118.*
Lloyed et al Modelling the human immune response: performance of a 1011 human antibody repertoire against a broad panel of therapeutically relevant antigens Protein Engineering, Design & Selection vol. 22 No. 3 pp. 159-168, 2009.*
Garcia et al How the T Cell Receptor Minireview Sees Antigen—A Structural View Cell, vol. 122, 333-336, Aug. 12, 2005.*
Janeway et al., Immunobiology, 5th Ed., Garland Science, 2001, pp. 106-108, 117-118 and 260-263.*
Manning et al., Effects of Complementarity Determining Region Mutations on the Affinity of an / T Cell Receptor:Measuring the Energy Associated with CD4/CD8 Repertoire SkewingJ. Exp. Med vol. 189, No. 3,, Feb. 1, 1999 461-470.*
Vajos et al Comprehensive Functional Maps of the Antigenbinding Site of an Anti-ErbB2 Antibody Obtained with Shotgun Scanning Mutagenesis J. Mol. Biol. (2002) 320, 415-428.*
International Search Report and Written Opinion dated May 19, 2016 from PCT/US2016/017521.
Van Rhijn et al., 2016, Genbank JQ778265.1.
Ahmadi, et al., "CD3 limits the efficacy of TCR gene therapy in vivo", Blood. 2011;118(13):3528-3537).
Anderson, et al., "Peptide Priming of Cytolytic Activity to HER-2 Epitope 369-377 in Healthy Individuals", 2000, Clinical Cancer Research 6:4192-4200.
Brossart, et al., "Her-2/neu-derived Peptides Are Tumor-associated Antigens Expressed by Human Renal Cell and Colon Carcinoma Lines and Are Recognized by in Vitro Induced Specific Cytotoxic T Lymphocytes", Cancer Research 58. 732-736. Feb. 15, 1998.

(Continued)

*Primary Examiner* — Maria G Leavitt
(74) *Attorney, Agent, or Firm* — Saul Ewing Arnstein & Lehr LLP; Kathryn Doyle

(57) ABSTRACT

The present invention relates to compositions and methods for treating HER2/Neu (ERBB2) expressing cancer cells. In some embodiments, the invention includes an isolated T cell receptor (TCR) having high affinity for and that specifically binds ERBB2$_{369-377}$ epitope on a target cell. Other embodiments include a T cell or a population of T cells modified to express ERBB2-specific TCR. Further embodiments include methods of using ERBB2-specific TCR gene transfer for treating ERBB2 expressing cancer cells. Also included are methods and pharmaceutical compositions comprising the modified T cells for adoptive therapy.

8 Claims, 8 Drawing Sheets
Specification includes a Sequence Listing.

(56) References Cited

OTHER PUBLICATIONS

Brossart, et al., "Induction of cytotoxic T-lymphocyte responses in vivo after vaccinations with peptide-pulsed dendritic cells", 2000, Blood 96(9):3102-3108.
Castilleja, et al., "Induction of Tumor-Reactive CTL by C-Side Chain Variants of the CTL Epitope HER-2/neu Protooncogene (369-377) Selected by Molecular Modeling of the Peptide: HLA-A2 Complex", J Immunol 2002; 169:3545-3554.
Cohen, et al., "Enhanced Antitumor Activity of Murine-Human Hybrid T-Cell Receptor (TCR) in Human Lymphocytes Is Associated with Improved Pairing and TCR/CD3 Stability", Cancer Res 2006; 66(17): 8878-86.
Cohen, et al., "Enhanced Antitumor Activity of T Cells Engineered to Express T-Cell Receptors with a Second Disulfide Bond", Cancer Res 2007;67(8):3898-903.
Collins, "Generation and initial analysis of more than 15,000 full-length human and mouse cDNA sequences.", 2002, PNAS 99(26):16899-16903.
Conrad, et al., "CTLs Directed against HER2 Specifically Cross-React with HER3 and HER4", J Immunol 2008; 180:8135-8145.
Cordaro, et al., "Can the Low-Avidity Self-Specific T Cell Repertoire Be Exploited for Tumor Rejection?", J Immunol 2002; 168:651-660.
Czerniecki, et al., "Targeting HER-2/neu in Early Breast Cancer Development Using Dendritic Cells with Staged Interleukin-12 Burst Secretion", Cancer Res 2007; 67: (4). Feb. 15, 2007.
Dangaj, et al., "Novel Recombinant Human B7-H4 Antibodies Overcome Tumoral Immune Escape to Potentiate T-Cell Antitumor Responses", Cancer Res; 73(15); 4820-9.
Han, et al., "Hla Class I Antigen Processing Machinery Component Expression and Intratumoral T-Cell Infiltrate as Independent Prognostic Markers in Ovarian Carcinoma", Clin Cancer Res. Jun. 1, 2008; 14(11): 3372-3379.
Henle, et al., "Enzymatic Discovery of a HER-2/neu Epitope That Generates Cross-Reactive T Cells", Immunol 2013; 190:479-488; Prepublished online Nov. 23, 2012.
Keogh, et al., "Identification of New Epitopes from Four Different Tumor-Associated Antigens: Recognition of Naturally Processed Epitopes Correlates with HLA-A*201-Binding Affinity", J Immunol 2001; 167:787-796.
Knutson, et al., "Immunization of Cancer Patients with a HER-2/neu, HLA-A2 Peptide, p. 369-377, Results in Short-lived Peptide-specific Immunity", Clin Cancer Res 2002;8:1014-1018.
Lanitis, et al., "A Human ErbB2-Specific T-Cell Receptor Confers Potent Antitumor Effector Functions in Genetically Engineered Primary Cytotoxic Lymphocytes", Human Gene Therapy 25:730-739 (Aug. 2014).
Lanitis, et al., "Primary Human Ovarian Epithelial Cancer Cells Broadly Express HER2 at Immunologically-Detectable Levels", 2012, PLoS One 7(11):e49829.
Liu, et al., "HER-2, gp100, and MAGE-1 Are Expressed in Human Glioblastoma and Recognized by Cytotoxic T Cells", Cancer Research 64, 4980-4986, Jul. 15, 2004.
Okamoto, et al., "Improved Expression and Reactivity of Transduced Tumor-Specific TCRs in Human Lymphocytes by Specific Silencing of Endogenous TCR", Cancer Res 2009;69(23):9003-11.
Peoples, et al., "Clinical Trial Results of a HER2/neu (E75) Vaccine to Prevent Recurrence in High-Risk Breast Cancer Patients", 2005, Journal of Clinical Oncology 23(30):7536-7545.
Rongcun, et al., "Identification of New HER2/neu-Derived Peptide Epitopes That Can Elicit Specific CTL Against Autologous and Allogeneic Carcinomas and Melanomas", J Immunol 1999; 163:1037-1044.
Sadelain, et al., "Targeting tumours with genetically enhanced T lymphocytes", Nat Rev Cancer 3(1):, 2003, 35-45.
Schumacher, et al., "Adoptive T cell therapy of cancer", Curr Opin Immunol. Apr. 2009 ; 21(2): 187-189.
Seliger, et al., "HER-2/neu Is Expressed in Human Renal Cell Carcinoma at Heterogeneous Levels Independently of Tumor Grading and Staging and Can Be Recognized by HLA-A2.1-Restricted Cytotoxic T Lymphocytes", Int. J. Cancer: 87, 349-359 (2000).
Willemsen, et al., "Genetic Engineering of T Cell Specificity for Immunotherapy of Cancer", Human Immunology, 54:, 2003, 56-68.
Xu, et al., "Rapid High Efficiency Sensitization of CD8+ T Cells to Tumor Antigens by Dendritic Cells Leads to Enhanced Functional Avidity and Direct Tumor Recognition Through an IL-12-Dependent Mechanism", J Immunol 2003; 171:2251-2261.
Zaks, et al., "Immunization with a Peptide Epitope (p369-377) from HER-2/neu Leads to Peptide-specific Cytotoxic T Lymphocytes That Fail to Recognize HER-2/neu+ Tumors", Cancer Research 58. 4902-4908. Nov. 1, 1998.
Zum Buschenfelde, et al., "Antihuman Epidermal Growth Factor Receptor 2 (HER2) Monoclonal Antibody Trastuzumab Enhances Cytolytic Activity of Class I-restricted HER2-specific T Lymphocytes Against HER2-overexpressing Tumor Cells", Cancer Research 62, 2244-2247, Apr. 15, 2002.
Accession AJL95220 dated Jan. 24, 2008.
Accession No. JC292637 dated Feb. 5, 2014.
European Patent Application No. 16752831.4—extended European Search Report dated Sep. 24, 2018.
Fisk, et al.,"Identification of an immunodominant Peptide of HER-2/neu Protooncogene Recognized by Ovarian Tumor-specific Cytotoxic T Lymphocyte Lines.", 1995, J Exp Med 181:2109-2117.

* cited by examiner

Fig. 3A
A. Untransduced SupT1 cells
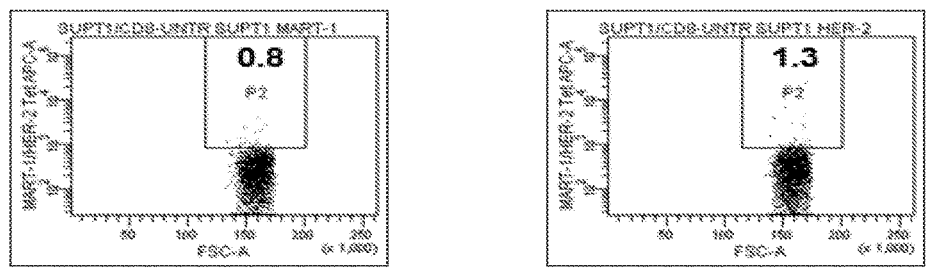
MART-1 SupT1 cells
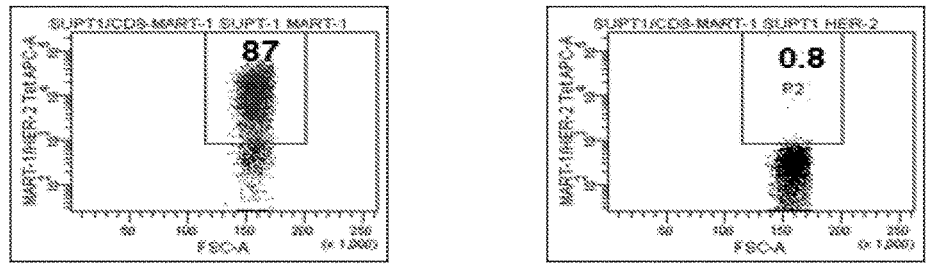
ErbB2 TCR2 SupT1 cells
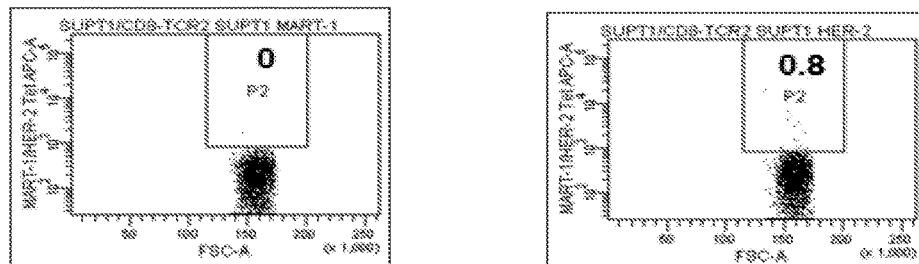
ErbB2 TCR7 SupT1 cells
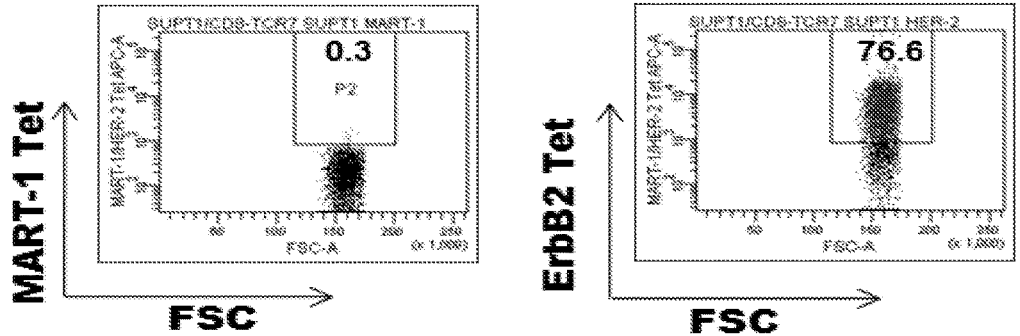

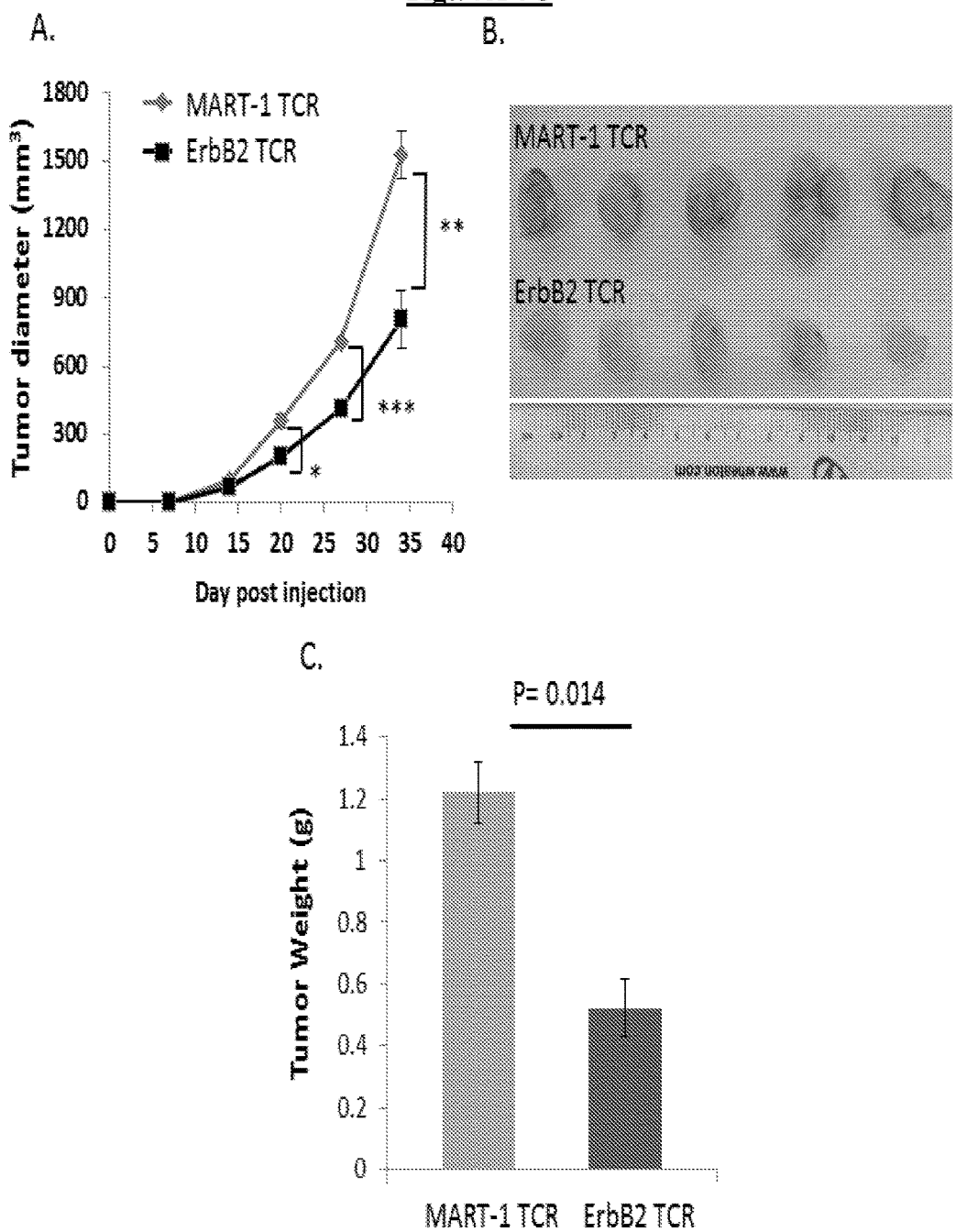

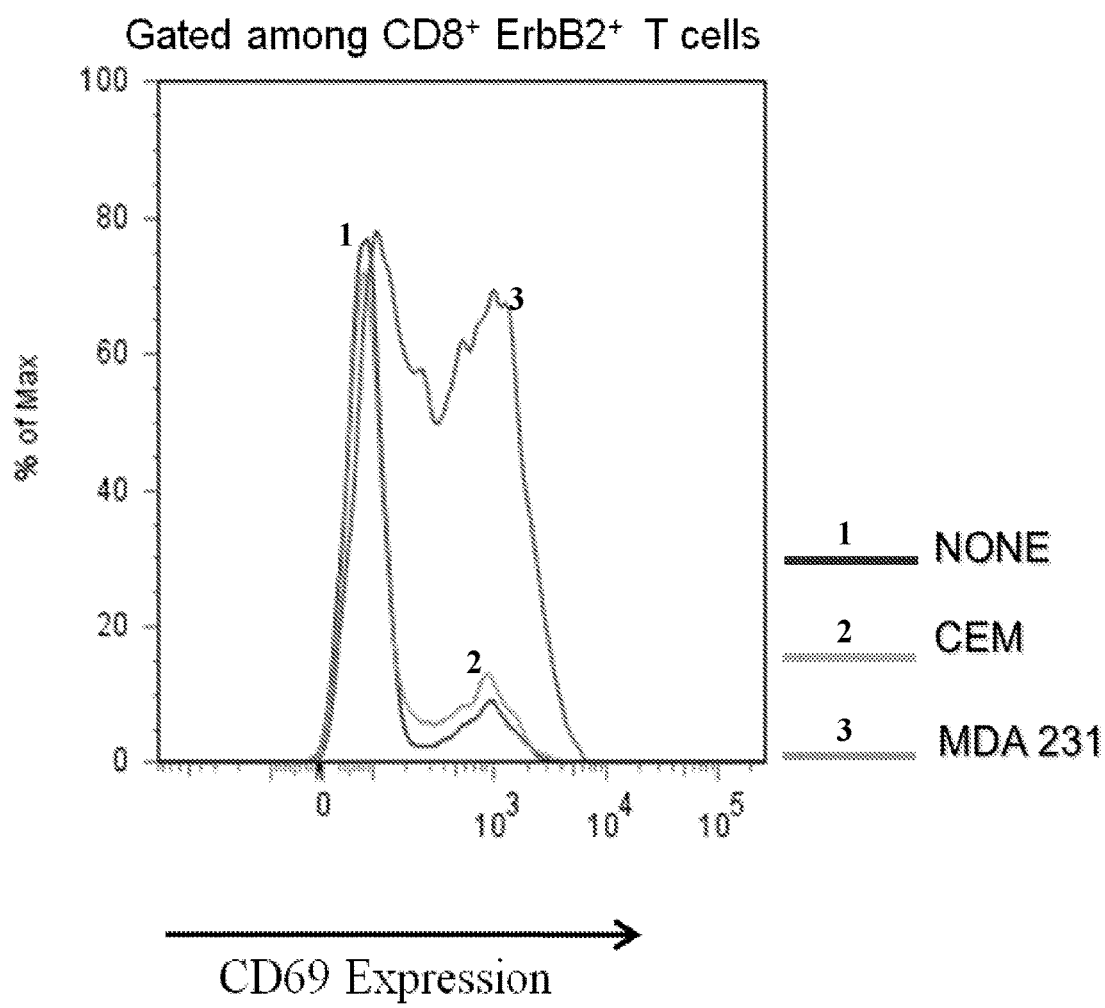

SEQUENCE LISTING

<160> NUMBER OF SEQ ID NOS: 9

<210> SEQ ID NO 1
<211> LENGTH: 810
<212> TYPE: DNA
<213> ORGANISM: Homo sapiens

<400> SEQUENCE: 1

```
atggcctctg cacccatctc gatgcttgcg atgctcttca cattgagtgg gctgagagct    60
cagtcagtgg ctcagccgga agatcaggtc aacgttgctg aagggaatcc tctgactgtg   120
aaatgcacct attcagtctc tggaaaccct tatctttttt ggtatgttca ataccccaac   180
cgaggcctcc agttccttct gaaatacatc acaggggata acctggttaa aggcagctat   240
ggctttgaag ctgaatttaa caagagccaa acctccttcc acctgaagaa ccatctgcc    300
cttgtgagcg actccgcttt gtacttctgt gctgtggaag atgccagact catgtttgga   360
gatggaactc agctggtggt gaagcccaat atccagaacc ctgaccctgc cgtgtaccag   420
ctgagagact ctaaatccag tgacaagtct gtctgcctat tcaccgattt tgattctcaa   480
acaaatgtgt cacaaagtaa ggattctgat gtgtatatca cagacaaaac tgtgctagac   540
atgaggtcta tggacttcaa gagcaacagt gctgtggcct ggagcaacaa atctgacttt   600
gcatgtgcaa acgccttcaa caacagcatt attccagaag acaccttctt ccccagccca   660
gaaagttcct gtgatgtcaa gctggtcgag aaaagctttg aaacagatac gaacctaaac   720
tttcaaaaacc tgtcagtgat tgggttccga atcctcctcc tgaaagtggc cgggtttaat   780
ctgctcatga cgctgcggct gtggtccagc                                    810
```

<210> SEQ ID NO 2
<211> LENGTH: 270
<212> TYPE: PRT
<213> ORGANISM: Homo sapiens

<400> SEQUENCE: 2

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Glu Asp Ala Arg Leu Met Phe Gly Asp Gly Thr Gln Leu Val Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
```

```
            210                 215                 220
Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Lys Val
                245                 250                 255

Ala Gly Phe Asn Leu Leu Met Thr Leu Arg Leu Trp Ser Ser
                260                 265                 270
```

<210> SEQ ID NO 3
<211> LENGTH: 936
<212> TYPE: DNA
<213> ORGANISM: Homo sapiens

<400> SEQUENCE: 3

```
atgggcttca ggctcctctg ctgtggtgcc ttctgcctcc tccaagcagg tcccttggac    60
acagctgttt cccagactcc aaaatacctg gtcacacaga tgggaaacga caagtccatt   120
aaatgtgaac aaaatctggg ccatgatact atgtattggt ataaacagga ctctaagaaa   180
tttctgaaga taatgtttag ctacaataat aaggagctca ttataaatga aacagttcca   240
aatcgcttct cacctaaatc tccagacaaa gctcacttaa atcttcacat caattccctg   300
gagcttggtg actctgctgt gtatttctgt gccagcagcc aactagcgga ctacaatgag   360
cagttcttcg ggccagggac acggctcacc gtgctagagg acctgaaaaa cgtgttccca   420
cccgaggtcg ctgtgtttga gccatcagaa gcagagatct cccacaccca aaaggccaca   480
ctggtgtgcc tggccacagg cttctacccc gaccacgtgg agctgagctg gtgggtgaat   540
gggaaggagg tgcacagtgg ggtcagcaca gacccgcagc ccctcaagga gcagcccgcc   600
ctcaatgact ccagatactg cctgagcagc cgcctgaggg tctcggccac cttctggcag   660
aaccccgca ccacttccg ctgtcaagtc cagttctacg ggctctcgga gaatgacgag   720
tggacccagg ataggcccaa acctgtcacc cagatcgtca gcgccgaggc ctggggtaga   780
gcagactgtg gcttcaccct cgagtcttac cagcaagggg tcctgtctgc caccatcctc   840
tatgagatct tgctagggaa ggccaccttg tatgccgtgc tggtcagtgc cctcgtgctg   900
atggctatgg tcaagagaaa ggattccaga ggctag                             936
```

<210> SEQ ID NO 4
<211> LENGTH: 311
<212> TYPE: PRT
<213> ORGANISM: Homo sapiens

<400> SEQUENCE: 4

```
Met Gly Phe Arg Leu Leu Cys Cys Gly Ala Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
                100                 105                 110
```

Ser Gln Leu Ala Asp Tyr Asn Glu Gln Phe Phe Gly Pro Gly Thr Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 5
<211> LENGTH: 1827
<212> TYPE: DNA
<213> ORGANISM: Homo sapiens

<400> SEQUENCE: 5
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatctttttt ggtatgttca ataccccaac     180
cgaggcctcc agttccttct gaaatacatc acaggggata acctggttaa aggcagctat     240
ggctttgaag ctgaatttaa caagagccaa acctccttcc acctgaagaa accatctgcc     300
cttgtgagcg actccgcttt gtacttctgt gctgtggaag atgccagact catgtttgga     360
gatggaactc agctggtggt gaagcccaat atccagaacc ctgaccctgc cgtgtaccag     420
ctgagagact ctaaatccag tgacaagtct gtctgcctat tcaccgattt tgattctcaa     480
acaaatgtgt cacaaagtaa ggattctgat gtgtatatca cagacaaaac tgtgctagac     540
atgaggtcta tggacttcaa gagcaacagt gctgtggcct ggagcaacaa atctgacttt     600
gcatgtgcaa acgccttcaa caacagcatt attccagaag acaccttctt ccccagccca     660
gaaagttcct gtgatgtcaa gctggtcgag aaaagctttg aaacagatac gaacctaaac     720
tttcaaaacc tgtcagtgat tgggttccga atcctcctcc tgaaagtggc cgggtttaat     780
ctgctcatga cgctgcggct gtggtccagc cgggccaagc ggtccggatc cggagccacc     840
aacttcagcc tgctgaagca ggccggcgac gtggaggaga ccccggcccc atgggcttc     900 aggctcctct gctgtggtgc cttctgcctc tccaagcag gtcccttgga cacagctgtt     960

```
tcccagactc caaaataccT ggtcacacag atgggaaacg acaagtccat taaatgtgaa    1020
caaaatctgg gccatgatac tatgtattgg tataaacagg actctaagaa atttctgaag    1080
ataatgttta gctacaataa taaggagctc attataaatg aaacagttcc aaatcgcttc    1140
tcacctaaat ctccagacaa agctcactta aatcttcaca tcaattccct ggagcttggt    1200
gactctgctg tgtatttctg tgccagcagc caactagcgg actacaatga gcagttcttc    1260
gggccaggga cacggctcac cgtgctagag gacctgaaaa acgtgttccc acccgaggtc    1320
gctgtgtttg agccatcaga agcagagatc tcccacaccc aaaaggccac actggtgtgc    1380
ctggccacag gcttctaccc cgaccacgtg gagctgagct ggtgggtgaa tgggaaggag    1440
gtgcacagtg gggtcagcac agacccgcag cccctcaagg agcagcccgc cctcaatgac    1500
tccagatact gcctgagcag ccgcctgagg gtctcggcca ccttctggca gaaccccgc     1560 aaccacttcc gctgtcaagt ccagttctac gggctctcgg agaatgacga gtggaccca g   1620 gatagggcca aacctgtcac ccagatcgtc agcgccgagg cctggggtag agcagactgt    1680
ggcttcacct ccgagtctta ccagcaaggg gtcctgtctg ccaccatcct ctatgagatc    1740
ttgctaggga aggccacctt gtatgccgtg ctggtcagtg ccctcgtgct gatggctatg    1800
gtcaagagaa aggattccag aggctag                                        1827
```

<210> SEQ ID NO 6
<211> LENGTH: 272
<212> TYPE: PRT
<213> ORGANISM: Homo sapiens

<400> SEQUENCE: 6

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Glu Asp Ala Arg Leu Met Phe Gly Asp Gly Thr Gln Leu Val Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
```

```
            210                 215                 220
Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Lys Val
                245                 250                 255

Ala Gly Phe Asn Leu Leu Met Thr Leu Arg Leu Trp Ser Ser Arg Ala
                260                 265                 270

<210> SEQ ID NO 7
<211> LENGTH: 312
<212> TYPE: PRT
<213> ORGANISM: Homo sapiens

<400> SEQUENCE: 7

Pro Met Gly Phe Arg Leu Leu Cys Cys Gly Ala Phe Cys Leu Leu Gln
1               5                   10                  15

Ala Gly Pro Leu Asp Thr Ala Val Ser Gln Thr Pro Lys Tyr Leu Val
                20                  25                  30

Thr Gln Met Gly Asn Asp Lys Ser Ile Lys Cys Glu Gln Asn Leu Gly
            35                  40                  45

His Asp Thr Met Tyr Trp Tyr Lys Gln Asp Ser Lys Lys Phe Leu Lys
50                  55                  60

Ile Met Phe Ser Tyr Asn Asn Lys Glu Leu Ile Ile Asn Glu Thr Val
65                  70                  75                  80

Pro Asn Arg Phe Ser Pro Lys Ser Pro Asp Lys Ala His Leu Asn Leu
                85                  90                  95

His Ile Asn Ser Leu Glu Leu Gly Asp Ser Ala Val Tyr Phe Cys Ala
                100                 105                 110

Ser Ser Gln Leu Ala Asp Tyr Asn Glu Gln Phe Phe Gly Pro Gly Thr
            115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
            290                 295                 300

Val Lys Arg Lys Asp Ser Arg Gly
305                 310
```

<210> SEQ ID NO 8
<211> LENGTH: 1255
<212> TYPE: PRT
<213> ORGANISM: Homo sapiens

<400> SEQUENCE: 8

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

```
Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
        420                 425                 430

Gly Arg Ile Leu His Asn Gly Ala Tyr Ser Leu Thr Leu Gln Gly Leu
    435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800
```

```
Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
        820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
```

```
                    1205                1210                1215

Asn Leu Tyr Tyr Trp Asp Gln Asp Pro Pro Glu Arg Gly Ala Pro
        1220                1225                1230

Pro Ser Thr Phe Lys Gly Thr Pro Thr Ala Glu Asn Pro Glu Tyr
        1235                1240                1245

Leu Gly Leu Asp Val Pro Val
        1250                1255

<210> SEQ ID NO 9
<211> LENGTH: 9
<212> TYPE: PRT
<213> ORGANISM: Homo sapiens

<400> SEQUENCE: 9

Lys Ile Phe Gly Ser Leu Ala Phe Leu
1               5
```

FULLY-HUMAN T-CELL RECEPTOR SPECIFIC FOR THE 369-377 EPITOPE DERIVED FROM THE HER2/NEU (ERBB2) RECEPTOR PROTEIN

CROSS-REFERENCE TO RELATED APPLICATIONS

The present application is a 35 U.S.C. § 371 national phase application from, and claims priority to, International Application No. PCT/US 2016/017521, filed Feb. 11, 2016, which is entitled to priority under 35 U.S.C. § 119(e) to U.S. Provisional Patent Application No. 62/116,864, filed Feb. 16, 2015, all of which applications are incorporated herein by reference in their entireties.

STATEMENT REGARDING FEDERALLY SPONSORED RESEARCH OR DEVELOPMENT

This invention was made with government support under Grants Nos. CA152540, CA083638 and CA009140-37 awarded by the National Institutes of Health. The government has certain rights in the invention.

BACKGROUND OF THE INVENTION

The ERBB2 (Her-2/neu) proto-oncogene encodes a member of a group of epithelial tyrosine kinase receptors involved in the initiation and progression of diverse malignancies including breast, ovarian, and gastric cancers (Engel and Kaklamani, Drugs 67, 1329-1341, 2007; Wong et al., Gynecol Obstet Invest 40, 209-212, 1995). ERBB2 gene amplification and overexpression leads to uncontrolled cell growth and survival, increased colony formation, (Bartsch et al., BioDrugs 21, 69-77, 2007) and impaired DNA repair (Pietras et al., Oncogene 9, 1829-1838, 1994). Several different immunotherapeutic approaches directed against ERBB2-expressing breast and ovarian tumors have been developed to date. Anti-ERBB2 antibody based immunotherapies, such as the monoclonal antibody trastuzumab, may be used to treat breast cancer patients with ERBB2 overexpression, but this approach has not been as efficacious in ovarian cancer patients (Bookman et al., official journal of the Am. Soc. Clin. Onc. 21, 283-290, 2003). Additionally, cancer vaccines have been used to induce specific anti-tumor immunity, but they produced only weak T-cell responses and did not induce objective tumor regression (Knutson et al., J Clin Oncol 23, 7536-7545, 2002; Peoples et al., J Clin Oncol 23, 7536-7545, 2005).

A T cell receptor is a complex of membrane proteins that participate in the activation of T cells in response to the presentation of antigen. Stimulation of the TCR is triggered by major histocompatibility complex molecules (MHC) on antigen presenting cells that present antigen peptides to the T cells and bind to the TCR complexes to induce a series of intracellular signaling cascades. The TCR is generally composed of six different membrane bound chains that form the TCR heterodimer responsible for ligand recognition. TCRs exist in alpha/beta and gamma/delta forms, which are structurally similar but have distinct anatomical locations and functions. In one embodiment, the TCR comprises a TCR alpha and beta chain, such as the nucleic encoding the TCR comprises a nucleic acid encoding a TCR alpha and a TCR beta chain. In another embodiment, an alpha or beta chain or both comprises at least one N-deglycosylation. Each chain is composed of two extracellular domains, a variable and constant domain. In one embodiment, the TCR comprises at least one murine constant region. The constant domain is proximal to the cell membrane, followed by a transmembrane domain and a short cytoplasmic tail. In one embodiment, the co-stimulatory signaling domain is a 4-1BB co-stimulatory signaling domain. The variable domain contributes to the determination of the particular antigen and MHC molecule to which the TCR has binding specificity. In turn, the specificity of a T cell for a unique antigen-MHC complex resides in the particular TCR expressed by the T cell. Each of the constant and variable domains may include an intra-chain disulfide bond. In one embodiment, TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes. Functional alpha and gamma chain polypeptides are formed by rearranged V-J-C regions, whereas beta and delta chains consist of V-D-J-C regions. The extracellular constant domain includes a membrane proximal region and an immunoglobulin region.

TCR gene transfer has been developed over the last decade as a reliable method to generate large numbers of T-cells of a given antigen specificity for adoptive cellular therapy of viral infectious diseases, virus-associated malignancies, and cancer (Engels and Uckert, Mol Aspects Med 28, 115-142, 2007). The clinical feasibility of TCR gene therapy was first demonstrated in melanoma using a TCR specific for MART1, a commonly expressed melanoma antigen (Morgan et al., Science 314, 126-129, 2006). Adoptive transfer of MART1 TCR-transduced CD8+ T-cells used in fifteen patients resulted in durable engraftment of the transferred population and significant tumor regression in two patients, demonstrating a proof of concept of adoptive T-cell transfer (Morgan et al., Science 314, 126-129, 2006). A higher affinity MART-1-specific TCR that conferred improved functional avidity and clinical efficacy in melanoma was later identified, although with greater incidence of vitiligo, uveitis and hearing loss resulting from collateral destruction of normal melanocytes (Johnson et al., Immunol 177, 6548-6559, 2006; Johnson et al., J Blood 114, 535-546, 2009).

ERBB2-directed TCR gene therapy would appear to hold significant promise for common epithelial cancers. However, isolation of highly avid ERBB2-specific TCRs directly from cancer patients has been challenging and has not been tested clinically. One promising strategy to generate ERBB2-specific T-cells relies on vaccination of patients bearing ERBB2+ tumors with powerful immune regimens that can overcome immunological ERBB2 self-tolerance and prime preexisting T-cell immunity. Administration of an autologous, matured dendritic cell (DC) vaccine pulsed with ERBB2-derived HLA class I and II peptides to HLA-A2+ patients with ERBB2+ breast tumors was shown to efficiently prime ERBB2-specific T-cells, increase their frequency, and result in tumor regression in some patients in an ERBB2/DC vaccine study (Czerniecki et al., Cancer Res 67, 1842-1852, 2007). Although cytotoxic T-lymphocytes (CTLs) specific for various immunogenic ERBB2 peptides have been described, they often exhibit both poor functional avidity and tumor reactivity.

Therefore there is a need in the art for optimizing T cell based adoptive immunotherapy and for generating potent CD8+ T-cells highly specific for an ERBB2 epitope demonstrating high functional avidity and tumor reactivity against tumor cells expressing endogenous antigen. This invention addresses this need.

SUMMARY OF THE INVENTION

As described herein, the present invention relates to compositions and methods for treating HER2/Neu (ERBB2) expressing cancer.

One aspect of the invention includes a purified T cell receptor (TCR) having affinity for a surface antigen on a target cell. The TCR of the invention is a tyrosine-protein kinase HER2/Neu (ERBB2)-specific TCR that comprises at least one selected from the group consisting of a TCR alpha chain comprising SEQ ID NOs: 2 or 6 and a TCR beta chain comprising SEQ ID NOs: 4 or 7.

Another aspect of the invention includes a purified nucleic acid sequence encoding a T cell receptor (TCR) having affinity for a surface antigen on a target cell. The TCR of the invention is a tyrosine-protein kinase HER2/Neu (ERBB2)-specific TCR that is encoded by at least one nucleic acid sequence selected from the group consisting of a nucleic acid encoding a TCR alpha chain comprising SEQ ID NO: 1, a nucleic acid encoding a TCR beta chain comprising SEQ ID NO: 3 and a nucleic acid encoding linked TCR alpha and beta chains comprising SEQ ID NO: 5.

Another aspect of the invention includes a purified nucleic acid that comprises a nucleotide sequence which is complementary to at least one of nucleic acids of the above-recited purified nucleic acid sequence encoding a T cell receptor (TCR) having affinity for a surface antigen on a target cell.

Another aspect of the invention includes a purified nucleic acid that comprises a nucleotide sequence which hybridizes under stringent conditions to at least one of nucleic acids of the above-recited purified nucleic acid sequence encoding a T cell receptor (TCR) having affinity for a surface antigen on a target cell.

An additional aspect of the invention includes a recombinant expression vector that comprises at least one of the nucleic acids of the above-recited purified nucleic acid sequence encoding a T cell receptor (TCR) having affinity for a surface antigen on a target cell.

A further aspect of the invention includes a modified mammalian cell that comprises the above-recited recombinant expression vector.

Another aspect of the invention includes a population of cells that comprises the above-recited modified mammalian cell and wherein the cell is a tumor infiltrating lymphocyte (TIL).

A further aspect of the invention includes a pharmaceutical composition that comprises the above-recited purified T cell receptor (TCR), and a pharmaceutically acceptable carrier.

In yet another aspect, the invention includes a method of treating cancer in a mammal in need thereof. The method of the invention comprises administering to the mammal the above-recited purified T cell receptor (TCR), in an effective amount to treat cancer in the mammal.

In various embodiments of the above aspects or any other aspect of the invention delineated herein, the purified TCR binds an epitope of ERBB2 receptor protein comprising amino acids 369-377 ($ERBB2_{369-377}$) of SEQ ID NO: 9. In certain embodiments, the target cell of the invention is HLA-A2+. In certain embodiments, the TCR of the invention comprises at least one disulfide bond. In other embodiments, the TCR alpha and beta chains are connected by a peptide linker. In other embodiments, the nucleotide sequence of at least one of the TCR chains is codon optimized. In other embodiments, the modified mammalian cell of the invention is selected from the group consisting of a peripheral blood mononuclear cell, a cord blood cell, a primary T cell, and a cell of a T cell line. In yet other embodiments, the modified mammalian cell of the invention is a tumor infiltrating lymphocyte (TIL). In further embodiments, the cancer to be treated by the method of the invention is a cancer of the breast, ovary, stomach, kidney, colon, bladder, salivary gland, endometrium, pancreas or lung. In yet further embodiments, the mammal is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A: IFN-γ production of $ERBB2_{369-377}$-specific T-cells in response to peptide-pulsed targets. ERBB2 or MART1-specific T-cells were co-cultured with T2 cells loaded with HLA-A2-restricted $ERBB2_{369-377}$ or $MART1_{26-35}$ peptide for 18 hours. FIG. 2B: $ERBB2_{369-377}$-specific T-cells exhibit high avidity against the relevant peptide. $ERBB2_{369-377}$-specific T-cells were incubated for 18 hours with T2 cells pulsed with a range of titrated concentrations of $ERBB2_{369-377}$ peptide. MART1 T-cells served as negative control effector T-cells and T2 pulsed with the $MART1_{26-35}$ served as negative control target T-cells. FIG. 2C: ERBB2 or MART1-specific T-cells were cultured alone (none) or stimulated overnight with human HLA-A2-restricted $ERBB2^+$ established cancer cell lines. SKOV-3 (HLA-A2$^-$ $ERBB2^+$) and CEM (HLA-A2$^-$ $ERBB2^-$) served as negative control tumor targets. FIG. 2D: Antigen processing machinery (APM) expression of HLA-A2-restricted ERBB2-expressing tumor cell lines. The mRNA levels of human TAP1, TAP2, TAPASIN and TAP2 were quantified by real time PCR. mRNA levels are expressed as fold increase over the APM-negative T2 cell line. β-actin was used as an endogenous gene control. Results depict the mean±SD of triplicate wells. For all assays, IFN-γ was quantified from cell-free supernatants by ELISA and is reported as the mean concentration (pg/ml)±SEM of duplicate wells.

FIGS. 3A-3B are a series of graphs illustrating the expression of the ERBB2 TCR on retrovirally transduced SupT1 cells and $CD8^+$ T-cells. FIG. 3A: Screening of TCR α/β pairs by retroviral transduction of SupT1 cells. Retroviruses encoding eight different TCR combinations were screened for $ERBB2_{369-377}$ specificity by transduction of SupT1 cells. HLA-A2/$ERBB2_{369-377}$ tetramer staining of the genetically modified SupT1 cells was performed five days after transduction and analyzed by flow cytometry. Two representative SupT1 populations are shown, each bearing different TCRs whose alpha and beta chains were isolated from the ERBB2-specific polyclonal CD8$^+$ T-cells. Untransduced (NV) and MART1 SupT1 cells served as negative controls for HLA-A2/ERBB2$_{369-377}$ tetramer binding. FIG. 3B: HLA-A2/ERBB2$_{369-377}$ tetramer staining of primary TCR-transduced CD8$^+$ T-cells. CD8$^+$ T-cells transduced with either the ERBB2 TCR7 or the MART1 TCR and untransduced CD8$^+$ T-cells (NV) were stained with the indicated HLA-A2/peptide tetramers. Numbers represent the percentage of tetramer$^+$ cells.

FIG. 4A: ERBB2 or MART1 TCR transduced T-cells were co-cultured with T2 cells loaded with HLA-A2-restricted ERBB2$_{369-377}$ or with MART1$_{26-35}$ for 18 hours. FIG. 4B: ERBB2 or MART1 TCR transduced T-cells were cultured alone (none) or stimulated overnight with human HLA-A2-restricted ERBB2$^+$ established cancer cell lines. SKOV-3(HLA-A2$^-$ ERBB2$^+$) and CEM (HLA-A2$^-$ ERBB2$^-$) served as negative control tumor targets. FIG. 4C: CD8$^+$ T-cells transduced with the ERBB2$_{369-377}$-specific TCR as well as the control MART1 TCR were incubated 11 days after transduction for 18 hours with T2 cells pulsed with a range of titrated concentrations of ERBB2$_{369-377}$ peptide. T2 pulsed with MART1$_{26-35}$ peptide served as negative control target T-cells. For all assays, IFN-γ was quantified from cell-free supernatants by ELISA and is reported as the mean concentration (pg/ml)±SEM of duplicate wells.

FIGS. 5A-5C are a series of graphs and illustration validating that T-cells expressing ERBB2$_{369-377}$-specific TCR7 delay tumor growth in vivo. T-cells expressing ERBB2$_{369-377}$-specific TCR7 delay tumor growth in vivo. Retrovirally transduced ERBB2 TCR7 CD8$^+$ T-cells and the breast cancer cell line MDA231 were co-injected subcutaneously into the flank of NSG mice on Day 0. MART1-specific F5 TCR-transduced T-cells co-injected with MDA231 were used as controls. FIG. 5A: Tumor growth was determined by caliper measurement over time. Results are expressed as mean tumor volume (mm3±SEM) with n=5 for all groups. Statistical significance of p<0.05 is reported as *p=0.0495, p=0.0075, *p=0.0029. After 35 days tumors were resected, photographed (FIG. 5B), and measured for tumor weight (FIG. 5C). TCR, T-cell Receptor; NSG, NOD/SCID/γ-chain$^{-/-}$.

FIG. 7 is a graph indicating that ERBB2-expressing cancer cells stimulate an activated phenotype of ERBB2-specific T-cells. ERBB2-specific T-cells express the CD69 early activation antigen in response to ERBB2-specific stimulation. ERBB2-specific T-cells were cultured without target-cells (none) or with the indicated ERBB2-negative or -positive established tumor cell targets for 24 hours. After the incubation period, the T-cells were stained for CD8, ERBB2 tetramer and CD69 and analyzed by flow cytometry. CD8$^+$ ERBB2 tetramer$^+$ CD69$^+$ T-cells were then sorted using fluorescence-activated flow sorting (FACS).

DETAILED DESCRIPTION

Definitions

Figure 1:
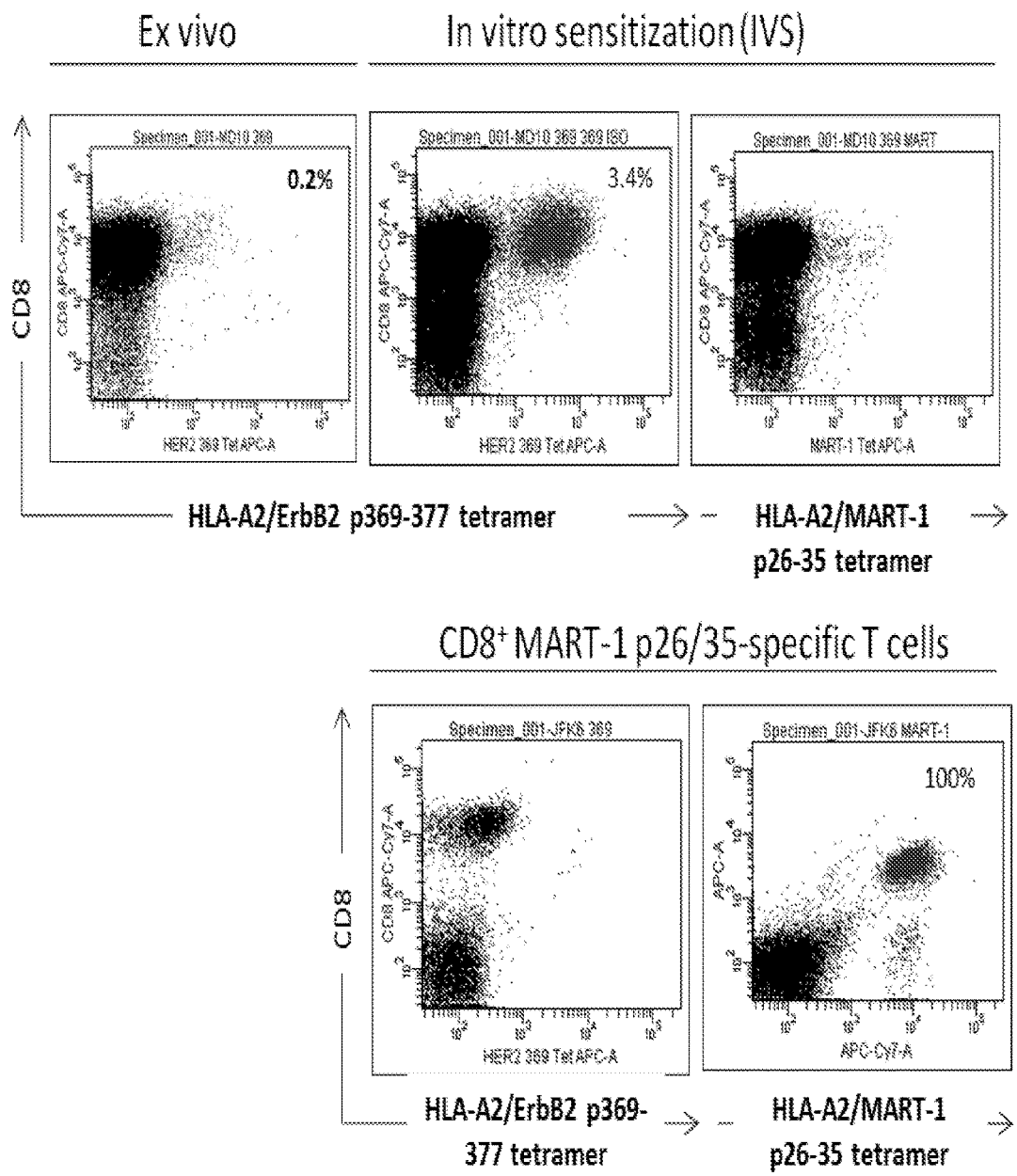
FIG. 1 is a series of graphs showing that ERBB2-pulsed DC1 increase the frequency of ERBB2-directed T-cells. $CD8^+$ T-cells were purified from a patient with ductal carcinoma in situ (DCIS) post administration of the ERBB2-pulsed-DC1 vaccine and co-cultured for 7 days with $ERBB2_{369-377}$ peptide-pulsed autologous dendritic cells. After 1 week, $CD8^+$ T-cells were harvested and analyzed via flow cytometry with labeled tetramer bound to $ERBB2_{369-377}$ or $MART1_{26-35}$. MART1 T-cells served as negative control effector cells. The percentage of positive cells for CD8 and ERBB2 are indicated on the dot plot.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "affinity", as used herein, refers to the capability of a ligand (e.g. a molecule, a protein, a hormone, a neurotransmitter or a drug) to form a coordination bond with a receptor. The binding affinity of a ligand with a receptor depends upon the interaction force of attraction between the ligand and its receptor binding site. High-affinity ligand binding results from greater intermolecular force between the ligand and its receptor and while low-affinity ligand binding involves less intermolecular force between the ligand and its receptor. High-affinity binding involves a longer residence time for the ligand at its receptor binding site than is the case for low-affinity binding. The binding affinity can be defined quantitatively by a dissociation constant (Kd), wherein the lower the Kd, the higher the binding affinity between a ligand and its receptor.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "codon optimization" as used herein is intended to refer to technique aimed to improve and maximize the protein expression in living organism by increasing the translational efficiency of gene of interest by transforming/replacing DNA sequence of nucleotides of one species into DNA sequence of nucleotides of another species. Codon optimization involves replacing wild type DNA sequences and rare codons by more highly expressed species sequences and frequently occurring codons without changing the protein.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

The term "electroporation" refers to the use of a transmembrane electric field pulse to induce microscopic pathways (pores) in a cellular membrane; their presence allows biomolecules such as plasmids, oligonucleotides (e.g. DNA, RNA), siRNA, drugs, ions, and water to pass from one side of the cellular membrane to the other.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" or "recombinant expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Fully human" refers to an immunoglobulin, such as an antibody, where the whole molecule is of human origin or consists of an amino acid sequence identical to a human form of the antibody.

By "hybridize" is meant pair to form a double-stranded molecule between complementary polynucleotide sequences (e.g., a gene described herein), or portions thereof, under variously stringent conditions (See e.g., Wahl and Berger, Methods Enzymol. 152:399, 1987; Kimmel, Methods Enzymol. 152:507, 1987). Under highly stringent conditions, a nucleotide sequence hybridizes to a target sequence in an amount that is detectably greater than the degree of hybridization observed under moderate or low stringent conditions. High stringency conditions include conditions that distinguish a polynucleotide with an exact complementary sequence, or one containing only a few scattered mismatches, from a random sequence that has only a few short regions (e.g., 3-10 bases) that match the nucleotide sequence to which it hybridizes. Conditions of high stringency require all (or most) bases of one polynucleotide to be paired with the complementary bases on the other, while conditions for low stringency allow some base mismatches.

Stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be achieved in the absence of organic solvent, e.g., formamide, while high stringency hybridization can be achieved in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a more preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions are defined by salt concentration and by temperature. Wash stringency can be increased by decreasing salt concentration or by increasing temperature. For example, stringent salt concentration for the wash steps are preferably less than about 30 mM NaCl and 3 mM trisodium citrate, and more preferably less than about 15 mM NaCl and 1.5 mM trisodium citrate. Stringent temperature conditions for the wash step will ordinarily include a temperature of at least about 25° C., more preferably of at least about 42° C., and even more preferably of at least about 68° C. In a preferred embodiment, wash steps are conducted at 25° C. in 30 mM NaCl, 3 mM trisodium citrate, and 0.1% SDS. In a more preferred embodiment, wash steps are conducted at 42° C. in 15 mM NaCl, 1.5 mM trisodium citrate, and 0.1% SDS. In a more preferred embodiment, wash steps are conducted at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "purified" as used herein means having been increased in purity, wherein "purity" is a relative term, and not to be necessarily construed as absolute purity. For example, the purity of a substance, for example, but not limited to a nucleic acid, can be at least about 50%, can be greater than 60%, 70%, 80%, 90%, 95%, or can be 100%. As used herein, a "purified" or "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antigen binding molecule, such as a TCR or an antibody, is meant an antigen binding molecule which recognizes a specific antigen, but does not substantially recognize or bind other molecules in a sample. For example, an antigen binding molecule that specifically binds to an antigen from one species may also bind to that antigen from one or more species. But, such cross-species reactivity does not itself alter the classification of an antigen binding molecule as specific. In another example, an antigen binding molecule that specifically binds to an antigen may also bind to different allelic forms of the antigen. However, such cross reactivity does not itself alter the classification of an antigen binding molecule as specific. In some instances, the terms "specific binding" or "specifically binding," can be used in reference to the interaction of an antigen binding molecule, an antibody, a protein, or a peptide with a second chemical species, to mean that the interaction is dependent upon the presence of a particular structure (e.g., an antigenic determinant or epitope) on the chemical species; for example, an antigen binding molecule or an antibody recognizes and binds to a specific protein structure rather than to proteins generally. If an antigen binding molecule (e.g. a TCR) is specific for epitope "A", the presence of a molecule containing epitope A (or free, unlabeled A), in a reaction containing labeled "A" and the antigen binding molecule, will reduce the amount of labeled A bound to the antigen binding molecule.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for treating HER2/Neu (ERBB2) expressing cancer cells. In some embodiments, the invention includes an isolated T cell receptor (TCR) having high affinity for and that specifically binds ERBB2$_{369-377}$ epitope on a target cell. Other embodiments include a T cell or a population of T cells modified to express ERBB2-specific TCR. Further embodiments include methods of using ERBB2-specific TCR gene transfer for treating ERBB2 expressing cancer cells.

T Cell Receptor

The present invention relates to a purified T cell receptor (TCR) having high affinity for and that specifically binds to a surface antigen on a target cell. In one embodiment, the TCR is a tyrosine-protein kinase HER2/Neu (ERBB2)-specific TCR. In another embodiment, the ERBB2-specific TCR comprises at least one selected from the group consisting of a TCR alpha chain comprising SEQ ID NOs: 2 or 6 and a TCR beta chain comprising SEQ ID NOs: 4 or 7.

In one embodiment, the invention provides a purified TCR having antigenic specificity for an epitope of ERBB2 receptor protein. In one embodiment, the TCR has high affinity for and specifically binds the epitope of ERBB2 comprising amino acids at position 369-377: KIFGSLAFL (SEQ ID NO: 9).

In one embodiment, the surface antigen (e.g. ERBB2) is presented on a HLA-A2+ target cell. Additional target cells include other HLA-A2+ alleles such as HLA-A*0201, HLA-A*0202, HLA-A*0203, HLA-A*0204, HLA-A*0205, HLA-A*0206, and/or HLA-A*0207 alleles (European Molecular Biology Laboratory, 2013).

In one embodiment, the present invention includes a purified nucleic acid comprising a nucleotide sequence encoding a T cell receptor (TCR) having high affinity for and specifically binds ERBB2 on a target cell. In other embodiment, the purified nucleic acid sequence encodes an ERBB2-specific TCR that comprising at least one selected from the group consisting of a TCR alpha chain, a TCR beta chain and linked TCR alpha and beta chains. In yet other embodiments, the nucleotide sequence encoding the TCR alpha chain is SEQ ID NO: 1, the nucleic acid sequence of the TCR beta chain is SEQ ID NO: 3 and the nucleic acid sequence of the linked TCR alpha and beta chains is SEQ ID NO: 5.

In one embodiment, at least one of the nucleotide sequences of the TCR chains is codon optimized to favor an increase in gene expression, translation efficiency and/or protein expression and in addition has a higher affinity for and/or more specifically binds ERBB2$_{369-377}$ (SEQ ID NO: 9). Such codon optimization strategies may include, but are not limited to, the modification of translation initiation regions, alteration of mRNA structural elements, and the use of different codon biases.

In one embodiment, the present invention relates to a purified nucleotide sequence which is complementary to at least one of the nucleotide sequences of the TCR chains, that is, complementary to SEQ ID NOs: 1, 3 or 5.

In one embodiment, the purified nucleic acid of the invention comprises a nucleotide sequence which hybridizes under stringent conditions to at least one of SEQ ID NOs: 1, 3 or 5. In another embodiment, the purified nucleic acid of the invention comprises a nucleotide sequence which hybridizes under highly stringent conditions to at least one of SEQ ID NOs: 1, 3 or 5.

In one embodiment, the nucleic acid of the present invention is incorporated into a recombinant expression vector. The invention provides recombinant expression vectors comprising any of the nucleic acids of the invention. The recombinant expression vector is any suitable recombinant expression vector known in the art, and can be used to transform or transfect any suitable cell. Suitable vectors include those designed for propagation and expansion or for expression or both, such as plasmids and viruses. In one embodiment, the recombinant expression vector is a viral vector, e.g., a retroviral vector such as a lentiviral vector.

The recombinant expression vectors of the invention can be prepared using standard recombinant DNA techniques (Sambrook et al., Molecular Cloning, A Laboratory Manual, 4th Edition, Cold Spring Harbor Laboratory Press, New York (2012)).

In other embodiments, the recombinant expression vector comprises regulatory sequences, such as transcription and translation initiation and termination codons. The recombinant expression vector can include one or more marker genes, which allow for selection of transformed or transfected hosts. Suitable marker genes include, for instance, neomycin/G418 resistance genes, hygromycin resistance genes, histidinol resistance genes, tetracycline resistance genes, and ampicillin resistance genes. The recombinant expression vector can comprise a promoter operably linked to the nucleotide sequence encoding the TCR or to the nucleotide sequence which is complementary to or which hybridizes to the nucleotide sequence encoding the TCR. A person skilled in the art can select the most suitable type of promoters such as, strong, weak, inducible, tissue-specific and developmental-specific. The promoter can be a non-viral promoter or a viral promoter, e.g., a cytomegalovirus (CMV) promoter, an SV40 promoter, an RSV promoter, and a promoter found in the long-terminal repeat of the murine stem cell virus (e.g. murine stem cell virus (MSCV)-based splice-gag vector (pMSGV) that utilizes a MSCV long terminal repeat (LTR) (Cohen et al., 2005)). The recombinant expression vector can be designed for either transient expression, for stable expression, or for both. Also, the recombinant expression vectors can be designed for constitutive expression or for inducible expression.

In one embodiment, the present invention includes a T cell comprising an exogenous T cell receptor (TCR). In one aspect, the invention includes a method for generating a modified T cell comprising expanding a population of T cells, and introducing a nucleic acid encoding a modified T cell receptor (TCR) comprising affinity for a surface antigen on a target cell into the expanded T cells. In this embodiment, the T cells are capable of expressing the modified TCR.

In one embodiment, the TCR comprises a wildtype TCR, a high affinity TCR, or a chimeric TCR. When the TCR is modified, it may have higher affinity for the target cell antigen than a wildtype TCR. In an embodiment where the TCR is a chimeric TCR, the TCR may include chimeric domains, such as a co-stimulatory signaling domain at a C' terminal of at least one of the amino acid chains of the TCR.

In another embodiment, the TCR may include a modified amino acid chain, such as a modified alpha or beta chain. Such modifications may include, but are not limited to, N-deglycosylation, altered domain (such as an engineered variable region to target a specific antigen or increase affinity), addition of one or more disulfide bonds, entire or fragment of a chain derived from a different species, and any combination thereof.

In one embodiment, the TCR may be expressed as a single protein comprising a linker peptide linking the alpha chain and the beta chain. In some embodiments, the alpha chain and the beta chain of the invention may further comprise a linker peptide. Nucleic acid encoding the linker peptide may advantageously facilitate the expression of the nucleic acid encoding the TCR in a host cell. In certain embodiments, the linker peptide may be cleaved following expression of the TCR in the host cell, resulting in separated alpha and beta chains in the cell. Non limiting examples of linker peptides include 2A-peptide and (GGGGS)n linkers.

Techniques for engineering and expressing T cell receptors include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In one aspect, the invention includes a population of modified T cells comprising a nucleotide sequence encoding a T cell receptor (TCR) comprising affinity for ERBB2 on a target cell, wherein the population of T cells is expanded prior to introduction therein of a nucleic acid encoding the TCR. In another aspect, the invention includes a population of modified T cells comprising a nucleotide sequence encoding a TCR having affinity for or specifically binding to ERBB2 on a target cell, wherein the population of T cells is expanded after the introduction therein of a nucleic acid encoding the TCR. In another aspect, the method of modifying the T cells includes transduction, transfection or electroporation of the cell. In yet another aspect, the method of modifying T cells can be any suitable method known in the art. Examples of methods of introducing nucleic acids into a T cell are described elsewhere herein.

Co-Stimulatory Molecule

In one embodiment, the modified T cell of the invention further includes a nucleic acid encoding a co-stimulatory molecule, such that the modified T cell expresses the co-stimulatory molecule. In certain embodiments, the co-stimulatory domain is selected from CD3, CD27, CD28, CD83, CD86, CD127, 4-1BB, 4-1BBL, PD1 and PD1L.

The nucleic acid may be introduced into the T cell by transducing the T cell, transfecting the T cell, or electroporating the T cell as described elsewhere herein.

Introduction of Nucleic Acids

Methods of introducing nucleic acids into a cell include physical, biological and chemical methods. Physical methods for introducing a polynucleotide, such as DNA or RNA into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells

Prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In one embodiment, the modified T cells are expanded prior to being modified to expressed ERBB2-specific TCR. In one embodiment, the extracellular domain portion of the chimeric membrane protein targets ERBB2. In another embodiment, the extracellular domain portion of the TCR targets specifically the epitope of ERBB2 receptor protein comprising amino acids 369-377 (ERBB2$_{369-377}$, SEQ ID NO: 9).

Expansion of T Cells

In one embodiment, expanding the T cells further includes culturing the T cells. In another embodiment, the source of the T cells to be expanded is peripheral blood mononuclear cells.

Generally, T cells are expanded by contact with a surface having attached thereto an agent that stimulates a CD3/TCR complex associated signal and a ligand that stimulates a co-stimulatory molecule on the surface of the T cells.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing the nucleic acid encoding the TCR into the T cell.

In one aspect, the method of expanding the T cells can further comprise isolating the T cells. In another embodiment, the invention further comprises cryopreserving the expanded T cells.

The culturing step as described herein can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the modified (e.g. transduced, transformed or electroporated) population.

In one embodiment, the method includes introducing a nucleic acid encoding a T cell receptor (TCR) comprising affinity for a surface antigen on a target cell into the expanded T cells. In another embodiment, the surface antigen on a target cell is an epitope of ERBB2 receptor protein comprising amino acids 369-377 (SEQ ID NO: 9).

In certain embodiments, the method further comprises stimulating the expanded T cells with at least one co-stimulatory molecule selected from the group consisting of CD3, CD27, CD28, CD83, CD86, CD127, 4-1BB, 4-1BBL, PD1 and PD1L. In yet other embodiments, the method of expanding the T cells can further comprise isolating the expanded T cells for further applications. In yet further embodiments, the modified, expanded T cells are cryopreserved after introduction with the nucleic acid encoding the TCR.

Therapy

The modified T cells described herein may be included in a composition for treatment of a subject. The composition may include a pharmaceutical composition and further include a pharmaceutically acceptable carrier. A therapeutically effective amount of the pharmaceutical composition comprising the modified T cells may be administered.

In one aspect, the invention includes a method for stimulating a T cell-mediated immune response to a target cell or tissue in a subject comprising administering to a subject an effective amount of a modified T cell. In this embodiment, the T cell or T cell population has been modified to comprise a T cell receptor (TCR) specific for ERBB2$_{369-377}$ epitope expressed on the surface of a target cell. The modified T cell may be administered to induce lysis of the target cell or tissue, such as where the induced lysis is antibody-dependent cell-mediated cytotoxicity (ADCC).

In another aspect, the invention includes a method for adoptive cell transfer therapy comprising administering a population of modified T cells to a subject in need thereof to treat (or prevent) a cancer or an immune reaction that is adverse to the subject. The modified T cell or T cell population comprises a T cell receptor (TCR) specific for ERBB2$_{369-377}$ epitope expressed on the surface of a target cell.

Further, the modified T cells can be administered to an animal, preferably a mammal, even more preferably a human, to suppress a cancer or an immune reaction. In one aspect, the invention includes treating a condition, such as cancer, in a subject, comprising administering to the subject a therapeutically effective amount of a pharmaceutical composition comprising a population of modified T cells. In some embodiments, the condition or cancer to be treated relates to an abnormal expression of ERBB2.

Non-limiting examples of cancer include but are not limited to cancer of the breast, ovary, stomach, kidney, colon, bladder, prostate, cervix, salivary gland, endometrium, pancreas, lung, skin, bone and brain.

In another embodiment, the T cells described herein may be used for the manufacture of a medicament for the treatment of an immune response in a subject in need thereof.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, allogenic or xenogenic with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

The cells described herein can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise a modified T cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The precise amount of pharmaceutical compositions of the present invention to be administered can be determined by a physician with consideration of individual differences in age, weight, immune response, and condition of the patient (subject). It can generally be stated that a pharmaceutical composition comprising the modified T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 ml to 400 ml. In certain embodiments, T cells are activated from blood draws of 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, cells expanded and modified using the methods described herein, or other methods known in the art where T cells are expanded to therapeutic levels, are administered to a patient in conjunction with (e.g., before, simultaneously or following) any number of relevant treatment modalities, including but not limited to treatment with agents such as chemotherapeutic agents, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, and cytokines.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Cells.

Retroviral packaging was performed in immortalized normal fetal renal 293GP cells (Center of Cancer Research, National Cancer Institute, Bethesda, Md.). Human cell lines: ovarian cancer cell lines SKOV3, OVCAR3, OVCAR-2, and OV55-2, the human breast cancer cell lines MDA231, the melanoma cell lines 624 and 938, the human T-cell lymphoblastic lymphoma cell line SupT1, and the T2 lymphoblastoid cell line. Cell lines were maintained in RPMI-1640 (Invitrogen) supplemented with 10% (vol/vol) heat-inactivated fetal bovine serum (FBS), 2 mmol/l L-glutamine, 100 µg/ml penicillin, and 100 U/ml streptomycin. All cell lines were routinely tested for mycoplasma contamination.

Preparation of ERBB2 Peptide-Loaded Monocyte-Derived Dendritic Cells.

All patients underwent initial leukapheresis on Baxter CS3000 using monocyte enrichment settings in the Apheresis Unit at the Hospital of the University of Pennsylvania. Peripheral blood monocytes were obtained from patients post-vaccine by combined leukapheresis and elutriation. The monocytes were washed, counted, and cultured at $3 \times 10^6$/ml in sterile 24-well plates in RPMI medium supplemented with 10% Fetal Bovine Serum (FBS), 500 IU/ml of recombinant research grade human granulocyte-macrophage colony stimulating factor (GM-CSF) and 250 IU/ml of interleukin-4 (IL-4) for four days. On day 5, 1,000 units/ml of IFN-γ was added in the culture followed by overnight incubation at 37° C. On day 6, LPS was added at 10 ng/ml for 6 hours to complete maturation of the dendritic cells. The dendritic cells' DC1 phenotype was analyzed by flow cytometry using monoclonal antibodies against CD80, CD86, CD83 and CD40. Half of the DC1 were subsequently pulsed with HLA class I binding $ERBB2_{369-377}$-specific peptide and the other half with $ERBB2_{689-697}$ peptide for 2 hours. The cells were harvested 2 hours later, washed, counted and assessed for viability prior to co-culture with $CD8^+$ T-cells.

In Vitro $CD8^+$ T-Cell Priming with ERBB2 Peptide Pulsed Dendritic Cells (DC1).

Autologous ERBB2 peptide-loaded dendritic cells were co-cultured with column-purified post-vaccination $CD8^+$ T-cells at a ratio of 10:1 in 48-well plates. IL-2 (50 IU/ml) was added to the cultures on day 2. After 10 days of sensitization, the $CD8^+$ T-cells were harvested and restimulated with T2 cells pulsed with either relevant or irrelevant peptides or tumor cell lines. Supernatants were harvested after 24 hours and analyzed by ELISA.

Cytokine Release Assays.

Cytokine release assays were carried out by co-culture of $1\times10^5$ T-cells with $1\times10^5$ tumor cells or peptide-loaded T2 cells per well in triplicate in 96-well round-bottom plates in 200 ul complete media. For the preparation of peptide-loaded T2 APCs, the latter were resuspended at $1\times10^7$/ml and loaded with ERBB2 or MART1 peptides at various peptide concentrations (1 ng/ml-10 ug/ml) at 37° C. for 2 hours. T2 cells were then washed twice with PBS and resuspended at $1\times10^6$/ml with RPMI-1640 supplemented with 10% heat-inactivated FBS. After 20-24 hours, cell-free supernatants were assayed for presence of IFN-γ using the BioLegend ELISA MAX™ Deluxe kit.

Construction of Retroviral Vectors.

To identify the sequences of the TCR genes, a 5'-RACE-PCR (Kit) amplifying the variable regions of the TCRα and TCRβ-chains including CDR3 was performed with RNA isolated from the T-cell clones. RACE-PCR products were sequenced. TCRα and TCRβ-chains were linked by 2A peptide linker (TCRb-P2A-TCRa) and the complete constructs were cloned into the retroviral vector plasmid pMSGV1 vector backbone, a derivative of the vector pMSGV [murine stem cell virus (MSCV)-based splice-gag vector] that utilizes a MSCV long terminal repeat (LTR) (Cohen et al., J Immunol 175, 5799-5808, 2005).

Recombinant Retrovirus Production.

Replication-defective retroviral vectors were produced as previously described (Wargo et al., cancer immunology, immunotherapy: CII 58, 383-394, 2009). Briefly $1\times10^6$ of 293-GP cells (transient viral producer cells) in a 6-well plate were co-transfected with 1.5 μg of retroviral vector DNA from each of the constructs and 0.5 μg of envelope DNA (RD114) using the Lipofectamine 2000 reagent (Invitrogen) and Optimem medium (BD Biosciences). Media was changed to DMEM with 10% FBS after 18 hours and viral supernatants were harvested at the 48-hour time point.

Human T-Cell Transduction.

Primary human $CD8^+$ T-cells were purchased from the Human Immunology Core at University of Pennsylvania and were isolated from healthy volunteer donors following leukapheresis by negative selection. All specimens were collected under a University Institutional Review Board-approved protocol, and written informed consent was obtained from each donor. T-cells were plated at $1\times10^6$/ml in 24-well plates (Costar) in complete media (RPMI 1640 supplemented with 10% heat-inactivated FBS, 100 U/ml penicillin, 100 m/ml streptomycin sulfate, 10 mM HEPES), and stimulated with anti-CD3 and anti-CD28-mAbs coated beads as described by manufacturer (Invitrogen) (Levine et al., J Immunol 159, 5921-5930, 1997) for 18-24 h prior to transduction. For retroviral transduction, non-tissue culture-treated 12-well plates (Becton Dickinson Labware, Franklin Lakes, N.J.) were treated with 25 m/ml of recombinant retronectin at 4° C. as directed by the manufacturer (RetroNectin, Takara, Otsu, Japan). After an overnight incubation, the retronectin was removed and well were blocked with 2% BSA in PBS at room temperature for 30 minutes. The retroviral vector supernatant (2-3 ml) was then applied by centrifugation (2000×g for 2 hours) and removed by aspiration. $5\times10^5$ of stimulated T-cells were added to each well in a final volume of 1 ml RMPI growth medium. Plates were centrifuged for 10 min at 1000×g and incubated overnight. The transduction process was repeated the following day. After transduction, the cells were grown in RPMI with 10% FBS and human recombinant interleukin-2 (IL-2) (Novartis) was added every other day to 100 IU/ml final concentration. Cell density of $0.5-1\times10^6$ cells/ml was maintained.

Flow Cytometry.

To determine T-cell antigen specificity, $CD8^+$ T-cells were stained with anti-CD8-FITC and allophycocyanin (APC)-labeled $ERBB2_{369-377}$ or $MART1_{27-35}$ tetramer (Becton Dickinson, San Jose, Calif.). To assess T-cell activation phenotype, T-cells were stained with the above reagents plus a PerCPCy5.5-labeled anti-human CD69 mAb. Dendritic cell phenotype was assessed using CD14-PerCPCy5.5, CD11c-APC, HLA-DR-PE, CD80-FITC, CD86-FITC, CD83-FITC, and CD40-FITC. All antibodies were purchased from BD Biosciences.

Real Time PCR.

RT-PCR was used to analyze the expression of human TAP1, TAP2, tapasin, LMP2 (APM components) in tumor cell lines. RNA was firstly isolated from tumor cells using the RNA easy kit (Qiagen). cDNA was then generated from 1 ug of RNA using First Strand Ready-To-Go beads (GE Healthcare). Real-time PCR was then performed in triplicates using Applied Biosystem's taqman primers specific for TAP1, TAP2, tapasin, LMP2 and β-actin. mRNA levels were normalized to β-actin and compared to mRNA levels of APM-deficient T2 cells. Data are presented as fold mRNA level.

Xenograft Model of Breast Cancer.

All animals were obtained from the Stem Cell and Xenograft Core of the Abramson Cancer Center, University of Pennsylvania. Mice were bred, treated, and maintained under pathogen-free conditions in-house under University of Pennsylvania IACUC approved protocols. For in vivo T-cell functional assessment, 6-12-week-old female NSG mice were subcutaneously injected on the flank with $1\times10^6$ MDA231 cells previously mixed with $1\times10^6$ ERBB2-specific T-cells in 0.2 ml PBS. Control mice were injected with MDA231 tumor cells mixed with $1\times10^6$ MART1-specific T-cells. Each group consisted of 5 mice. Tumor growth was determined by caliper measurement over time and tumor volumes calculated using the formula $V=\frac{1}{2}(length\times width)$, where length is the greatest longitudinal diameter and width is the greatest transverse diameter. Mice were terminated after 40 days or earlier if they became distressed and moribund. Following termination, tumors were resected, photographed, and weighted.

Statistical Analysis.

GraphPad Prism 4.0 (GraphPad Software) was used for the statistical analysis.

```
                        Sequences (5'-3')

TCR alpha Chain (TCR AV3)
SEQ ID NO: 1 (Nucleic acid)
ATGGC CTCTG CACCC ATCTC GATGC TTGCG ATGCT CTTCA CATTG
AGTGG GCTGA GAGCT CAGTC AGTGG CTCAG CCGGA AGATC AGGTC
AACGT TGCTG AAGGG AATCC TCTGA CTGTG AAATG CACCT ATTCA
GTCTC TGGAA ACCCT TATCT TTTTT GGTAT GTTCA ATACC CCAAC
CGAGG CCTCC AGTTC CTTCT GAAAT ACATC ACAGG GGATA ACCTG
GTTAA AGGCA GCTAT GGCTT TGAAG CTGAA TTTAA CAAGA GCCAA
ACCTC CTTCC ACCTG AAGAA ACCAT CTGCC CTTGT GAGCG ACTCC
GCTTT GTACT TCTGT GCTGT GGAAG ATGCC AGACT CATGT TTGGA
GATGG AACTC AGCTG GTGGT GAAGC CCAAT ATCCA GAACC CTGAC
CCTGC CGTGT ACCAG CTGAG AGACT CTAAA TCCAG TGACA AGTCT
GTCTG CCTAT TCACC GATTT TGATT CTCAA ACAAA TGTGT CACAA
AGTAA GGATT CTGAT GTGTA TATCA CAGAC AAAAC TGTGC TAGAC
ATGAG GTCTA TGGAC TTCAA GAGCA ACAGT GCTGT GGCCT GGAGC
AACAA ATCTG ACTTT GCATG TGCAA ACGCC TTCAA CAACA GCATT
ATTCC AGAAG ACACC TTCTT CCCCA GCCCA GAAAG TTCCT GTGAT
GTCAA GCTGG TCGAG AAAAG CTTTG AAACA GATAC GAACC TAAAC
TTTCA AAACC TGTCA GTGAT TGGGT TCCGA ATCCT CCTCC TGAAA
GTGGC CGGGT TTAAT CTGCT CATGA CGCTG CGGCT GTGGT CCAGC SEQ ID NO: 2 (Amino acid)
MASAPISMLAMLFTLSGLRAQSVAQPEDQVNVAEGNPLTVKCTYSVSGNPYLF
WYVQYPNRGLQFLLKYITGDNLVKGSYGFEAEFNKSQTSFHLKKPSALVSDSA
LYFCAVEDARLMFGDGTQLVVKPNIQNPDPAVYQLRDSKSSDKSVCLFTDFDS
QTNVSQSKDSDVYITDKTVLDMRSMDFKSNSAVAWSNKSDFACANAFNNSIIP
EDTFFPSPESSCDVKLVEKSFETDTNLNFQNLSVIGFRILLLKVAGFNLLMTLRL
WSS TCR beta chain (TCR BV3-1 (CB2))
SEQ ID NO: 3 (Nucleic acid)
ATGG GCTTC AGGCT CCTCT GCTGT GGTGC CTTCT GCCTC CTCCA AGCAG
GTCCC TTGGA CACAG CTGTT TCCCA GACTC CAAAA TACCT GGTCA
CACAG ATGGG AAACG ACAAG TCCAT TAAAT GTGAA CAAAA TCTGG
GCCAT GATAC TATGT ATTGG TATAA ACAGG ACTCT AAGAA ATTTC
TGAAG ATAAT GTTTA GCTAC AATAA TAAGG AGCTC ATTAT AAATG
AAACA GTTCC AAATC GCTTC TCACC TAAAT CTCCA GACAA AGCTC
ACTTA AATCT TCACA TCAAT TCCCT GGAGC TTGGT GACTC TGCTG
TGTAT TTCTG TGCCA GCAGC CAACT AGCGG ACTAC AATGA GCAGT
TCTTC GGGCC AGGGA CACGG CTCAC CGTGC TAGAG GACCT GAAAA
ACGTG TTCCC ACCCG AGGTC GCTGT GTTTG AGCCA TCAGA AGCAG
AGATC TCCCA CACCC AAAAG GCCAC ACTGG TGTGC CTGGC CACAG
GCTTC TACCC CGACC ACGTG GAGCT GAGCT GGTGG GTGAA TGGGA
AGGAG GTGCA CAGTG GGGTC AGCAC AGACC CGCAG CCCCT CAAGG
AGCAG CCCGC CCTCA ATGAC TCCAG ATACT GCCTG AGCAG CCGCC
TGAGG GTCTC GGCCA CCTTC TGGCA GAACC CCCGC AACCA CTTCC
GCTGT CAAGT CCAGT TCTAC GGGCT CTCGG AGAAT GACGA GTGGA
CCCAG GATAG GGCCA AACCT GTCAC CCAGA TCGTC AGCGC CGAGG
CCTGG GGTAG AGCAG ACTGT GGCTT CACCT CCGAG TCTTA CCAGC
AAGGG GTCCT GTCTG CCACC ATCCT CTATG AGATC TTGCT AGGGA
AGGCC ACCTT GTATG CCGTG CTGGT CAGTG CCCTC GTGCT GATGG
CTATG GTCAA GAGAA AGGAT CCAGG AGGCT AG SEQ ID NO: 4 (Amino acid)
MGFRLLCCGAFCLLQAGPLDTAVSQTPKYLVTQMGNDKSIKCEQNLGHDTMY
WYKQDSKKFLKIMFSYNNKELIINETVPNRFSPKSPDKAHLNLHINSLELGDSA
VYFCASSQLADYNEQFFGPGTRLTVLEDLKNVFPPEVAVFEPSEAEISHTQKAT
LVCLATGFYPDHVELSWWVNGKEVHSGVSTDPQPLKEQPALNDSRYCLSSRL
RVSATFWQNPRNHFRCQVQFYGLSENDEWTQDRAKPVTQIVSAEAWGRADC
GFTSESYQQGVLSATILYEILLGKATLYAVLVSALVLMAMVKRKDSRG TCR alpha chain (TCR AV3) and TCR beta chain (TCR BV3-1 (CB2)) linked
SEQ ID NO: 5 (Nucleic acid)
ATGGC CTCTG CACCC ATCTC GATGC TTGCG ATGCT CTTCA CATTG
AGTGG GCTGA GAGCT CAGTC AGTGG CTCAG CCGGA AGATC AGGTC
AACGT TGCTG AAGGG AATCC TCTGA CTGTG AAATG CACCT ATTCA
GTCTC TGGAA ACCCT TATCT TTTTT GGTAT GTTCA ATACC CCAAC
CGAGG CCTCC AGTTC CTTCT GAAAT ACATC ACAGG GGATA ACCTG
GTTAA AGGCA GCTAT GGCTT TGAAG CTGAA TTTAA CAAGA GCCAA
ACCTC CTTCC ACCTG AAGAA ACCAT CTGCC CTTGT GAGCG ACTCC
GCTTT GTACT TCTGT GCTGT GGAAG ATGCC AGACT CATGT TTGGA
GATGG AACTC AGCTG GTGGT GAAGC CCAAT ATCCA GAACC CTGAC
CCTGC CGTGT ACCAG CTGAG AGACT CTAAA TCCAG TGACA AGTCT
```

| Sequences (5'-3') |
|---|
| GTCTG CCTAT TCACC GATTT TGATT CTCAA ACAAA TGTGT CACAA<br>AGTAA GGATT CTGAT GTGTA TATCA CAGAC AAAAC TGTGC TAGAC<br>ATGAG GTCTA TGGAC TTCAA GAGCA ACAGT GCTGT GGCCT GGAGC<br>AACAA ATCTG ACTTT GCATG TGCAA ACGCC TTCAA CAACA GCATT<br>ATTCC AGAAG ACACC TTCTT CCCCA GCCCA GAAAG TTCCT GTGAT<br>GTCAA GCTGG TCGAG AAAAG CTTTG AAACA GATAC GAACC TAAAC<br>TTTCA AAACC TGTCA GTGAT TGGGT TCCGA ATCCT CCTCC TGAAA<br>GTGGC CGGGT TTAAT CTGCT CATGA CGCTG CGGCT GTGGT CCAGC<br>CGGGC CAAGC GGTCC GGATC CGGAG CCACC AACTT CAGCC TGCTG<br>AAGCA GGCCG GCGAC GTGGA GGAGA ACCCC GGCCC CATGG GCTTC<br>AGGCT CCTCT GCTGT GGTGC CTTCT GCCTC CTCCA AGCAG GTCCC<br>TTGGA CACAG CTGTT TCCCA GACTC CAAAA TACCT GGTCA CACAG<br>ATGGG AAACG ACAAG TCCAT TAAAT GTGAA CAAAA TCTGG GCCAT<br>GATAC TATGT ATTGG TATAA ACAGG ACTCT AAGAA ATTTC TGAAG<br>ATAAT GTTTA GCTAC AATAA TAAGG AGCTC ATTAT AAATG AAACA<br>GTTCC AAATC GCTTC TCACC TAAAT CTCCA GACAA AGCTC ACTTA<br>AATCT TCACA TCAAT TCCCT GGAGC TTGGT GACTC TGCTG TGTAT<br>TTCTG TGCCA GCAGC CAACT AGCGG ACTAC AATGA GCAGT TCTTC<br>GGGCC AGGGA CACGG CTCAC CGTGC TAGAG GACCT GAAAA ACGTG<br>TTCCC ACCCG AGGTC GCTGT GTTTG AGCCA TCAGA AGCAG AGATC<br>TCCCA CACCC AAAAG GCCAC ACTGG TGTGC CTGGC CACAG GCTTC<br>TACCC CGACC ACGTG GAGCT GAGCT GGTGG GTGAA TGGGA AGGAG<br>GTGCA CAGTG GGGTC AGCAC AGACC CGCAG CCCCT CAAGG AGCAG<br>CCCGC CCTCA ATGAC TCCAG ATACT GCCTG AGCAG CCGCC TGAGG<br>GTCTC GGCCA CCTTC TGGCA GAACC CCCGC AACCA CTTCC GCTGT<br>CAAGT CCAGT TCTAC GGGCT CTCGG AGAAT GACGA GTGGA CCCAG<br>GATAG GGCCA AACCT GTCAC CCAGA TCGTC AGCGC CGAGG CCTGG<br>GGTAG AGCAG ACTGT GGCTT CACCT CCGAG TCTTA CCAGC AAGGG<br>GTCCT GTCTG CCACC ATCCT CTATG AGATC TTGCT AGGGA AGGCC<br>ACCTT GTATG CCGTG CTGGT CAGTG CCCTC GTGCT GATGG CTATG<br>GTCAA GAGAA AGGAT TCCAG AGGCT AG |

The highlighted nucleotide region above links the TCR alpha and beta chains and contains a Furin cleavage sequence region (dark grey color) and P2A skip sequence (light grey color).

Of note is the Furin cleavage region results in the removal of the P2A-derived amino acid residues (The P2A peptide is from PTV1, porcine teschovirus-1)

TCR alpha chain (post P2A cleavage)
(Amino acid)
SEQ ID NO : 6

MASAPISMLAMLFTLSGLRAQSVAQPEDQVNVAEGNPLTVKCTYSVSG

NPYLFWYVQYPNRGLQFLLKYITGDNLVKGSYGFEAEFNKSQTSFHLK

KPSALVSDSALYFCAVEDARLMFGDGTQLVVKPNIQNPDPAVYQLRDS

KSSDKSVCLFTDFDSQTNVSQSKDSDVYITDKTVLDMRSMDFKSNSAV

AWSNKSDFACANAFNNSIIPEDTFFPSPESSCDVKLVEKSFETDTNLN

FQNLSVIGFRILLLKVAGFNLLMTLRLWSSRA

TCR beta chain (post P2A cleavage)
(Amino acid)
SEQ ID NO: 7

PMGFRLLCCGAFCLLQAGPLDTAVSQTPKYLVTQMGNDKSIKCEQNLG

HDTMYWYKQDSKKFLKIMFSYNNKELIINETVPNRFSPKSPDKAHLNL

HINSLELGDSAVYFCASSQLADYNEQFFGPGTRLTVLEDLKNVFPPEV

AVFEPSEAEISHTQKA TLVCLATGFYPDHVELSWWVNGKEVHSGVS

TDPQPLKEQPALNDSRYCLSSRLRVSATFWQNPRNHFRCQVQFYGLS

ENDEWTQDRAKPVTQIVSAEAWGRADCGFTSESYQQGVLSATILYEIL

LGKATLYAVLVSALVLMAMVKRKDSRG

Receptor tyrosine-protein kinase ErbB-2 (ERBB2),
Homo sapiens (Uniprot P04626)
(Amino acid)
SEQ ID NO: 8

MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

-continued

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV

ERBB2-Epitope 669-677 ($ERBB2_{369-377}$)
(Amino acid)
SEQ ID NO: 9

KIFGSLAFL

Tables

Table 1: TCR α and β DNA Constructs

Top: TCR Vα/β usage of HLA-A2/ErbB2 multimer$^+$ CD69$^+$ CD8$^+$ T-cells. Twenty-three TCR α chain clones and fourteen TCR β chain clones were isolated from ErbB2-specific CD8$^+$ T-cells. The TRAV and TRBV repertoire was determined by sequencing. The number of repeats for each clone is shown on the right side of the table. Bottom: Eight different retroviral backbones encoding eight different TCR α/β combinations were constructed for the propagation of retroviral particles. TCR α and β chains that were presented more than once in the TCR repertoire were subcloned into the MSGV-1 retroviral backbones.

The results of the experiments are now described in the following examples.

Figure 6:
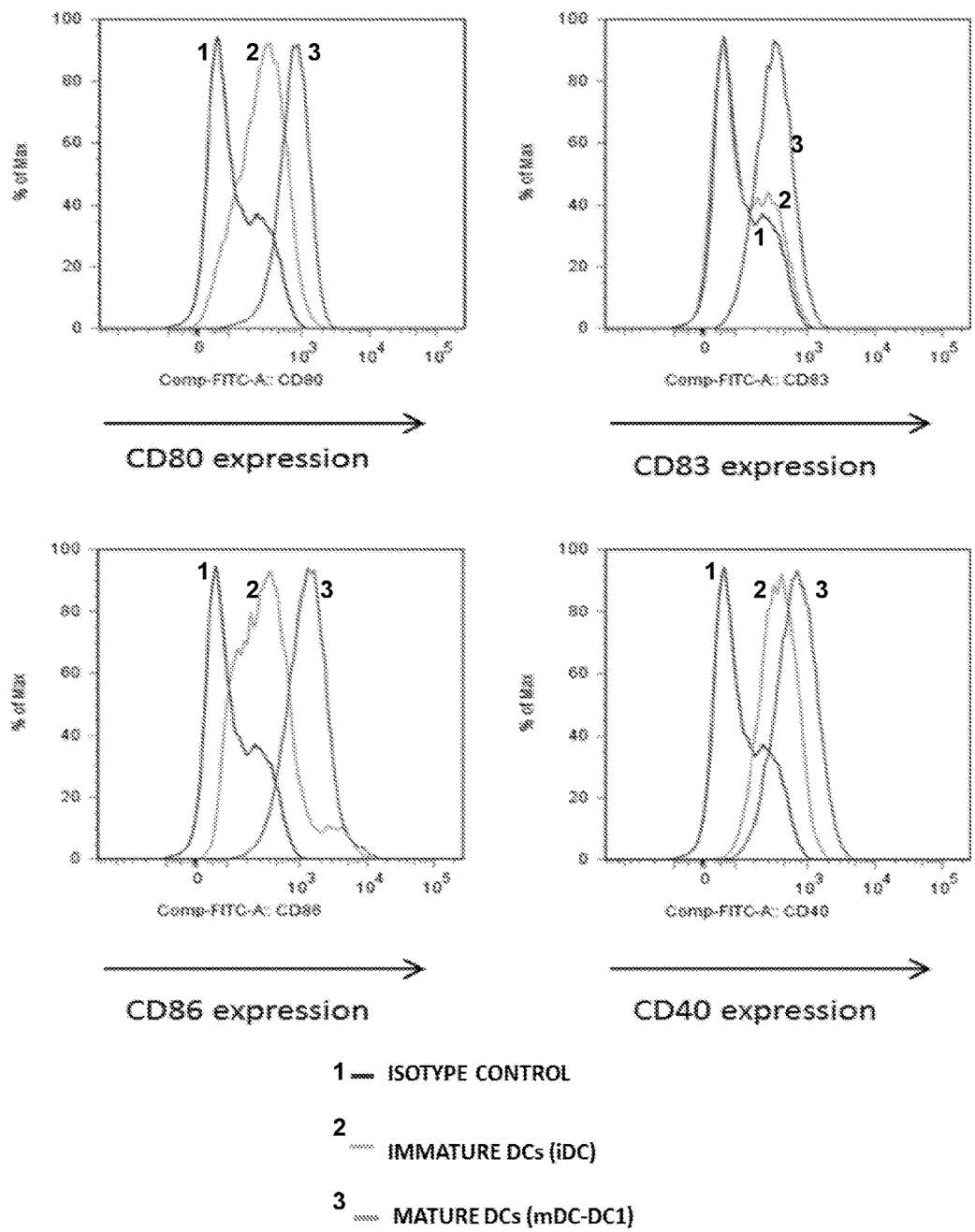
FIG. 6 is a series of graphs demonstrating that polarized DC1 cells exhibit characteristics of mature dendritic cells. Peripheral blood monocytes were differentiated to immature dendritic cells (iDCs) upon culture in complete medium in the presence of GM-CSF and IL-4 for four days. Mature dendritic cells (mDCs) were obtained upon stimulation of iDCs with IFN-γ and LPS. mDCs were harvested and assayed for their expression of CD80, CD86, CD83 and CD40 via flow cytometry analysis using specific antibodies. mDCs demonstrated high levels of expression of CD80, CD83, CD86 and CD40.

Example 1: Induction of ERBB2-specific CD8$^+$ T-Cells with ERBB2 Peptide-Loaded Dendritic Cells Peripheral blood monocytes and peripheral blood T cells were obtained from an HLA-A2+ patient (M10) that had previously been vaccinated with autologous dendritic cells (DCs) pulsed with a cocktail of HLA class I and class II peptides, including the HLA Class I-restricted $ERBB2_{369-377}$ peptide (Czerniecki et al., Cancer Res 67, 1842-1852, 2007). This patient's post-vaccination CD8+ T cells demonstrated a robust IFN-γ response against autologous DCs pulsed with $ERBB2_{369-377}$ peptide and against the HLA-A2+/ERBB2+ breast cancer cell line MDA231. Of note, the patient's pre-vaccination CD8+ T cells showed low levels of IFN-γ against either target, establishing evidence of a strong, vaccine-induced anti-ERBB2 response. The patient's peripheral blood monocytes were matured into DCs utilizing an in vitro protocol and showed relatively high expression levels of CD80, CD86, CD83 and CD40 (FIG. 6). The matured DCs were then pulsed with $ERBB2_{369-377}$ peptide and used for the in vitro stimulation of CD8+ T cells purified from the patient's post vaccination peripheral blood. Following 7 days of in vitro stimulation, nearly 3% of the viable CD8+ T cell population recognized the stimulating $ERBB2_{369-377}$ peptide as assessed by binding of an HLA-A2/$ERBB2_{369-377}$ tetramer (FIG. 1). This represented a 17-fold increase over 1 week, relative to the starting percentage of ERBB2-specific T-cells observed in the blood of the post-vaccinated patient. ERBB2-specific T-cells did not bind to MART-$1_{26-35}$ tetramer complexes, demonstrating their specificity for $ERBB2_{369-377}$ peptide. In contrast, MART-1 TCR transduced T-cells did not bind to $ERBB2_{369-377}$ tetramer complex, but exhibited strong binding to MART-$1_{26-35}$ tetramer complexes (FIG. 1). Collectively, ERBB2 peptide-loaded DCs were capable of boosting the frequency of $ERBB2_{369-377}$ peptide-specific T cells.

Figures 2A, 2B, 2C, 2D:
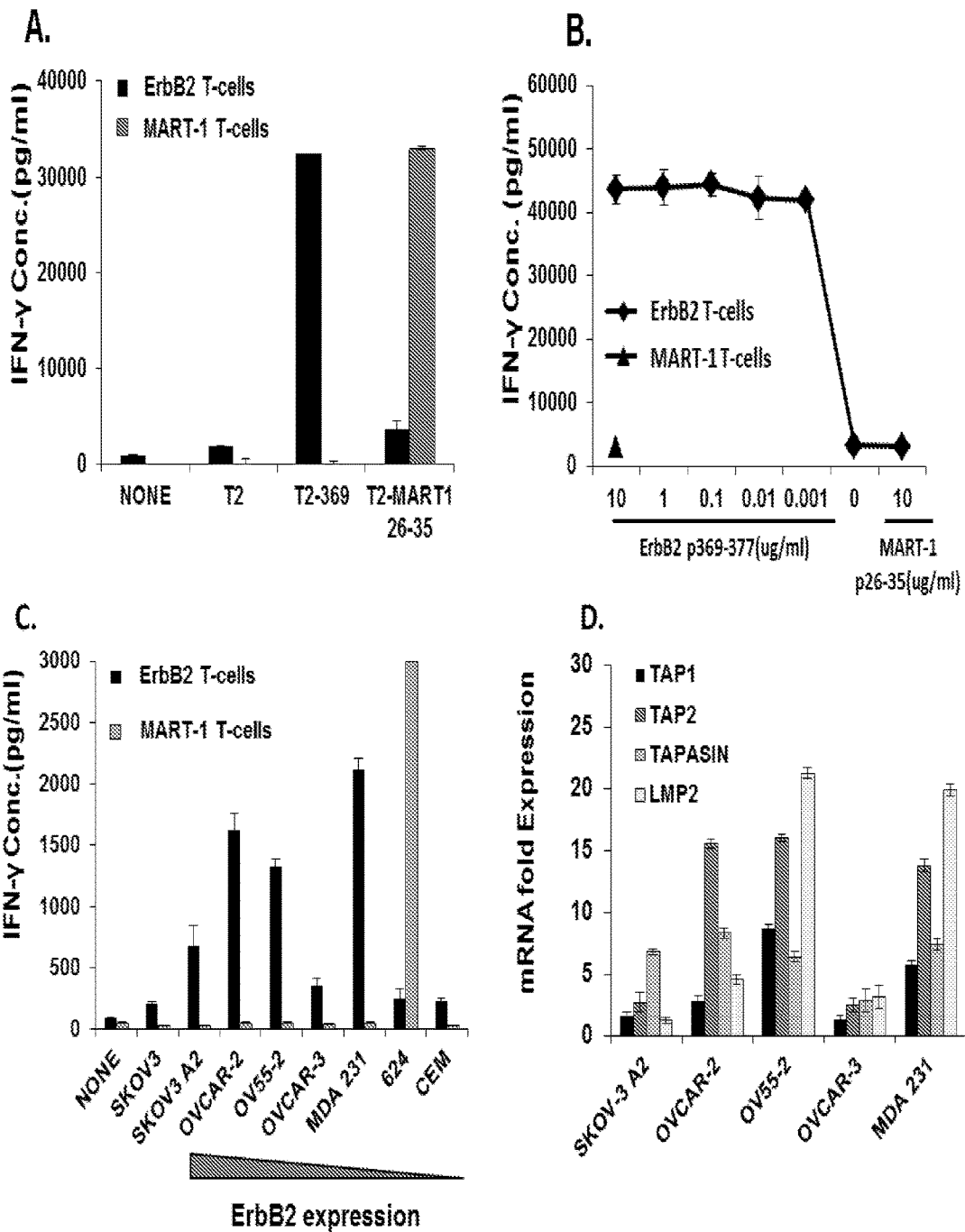
FIGS. 2A-2D are a series of histograms and graphs demonstrating that $ERBB2_{369-377}$-specific T-cells strongly recognize peptide-pulsed T2 cells and differentially recognize HLA-A2-restricted ERBB2-expressing tumor cells.

Example 2: ERBB2-Specific CD8$^+$ T-Cells Exert Potent Effector Functions Against ERBB2 Peptide-Loaded Targets and ERBB2-Expressing Cancer Cells To evaluate their effector functions, ERBB2-specific T-cells were initially exposed to HLA-A2+ T2 cells preloaded with $ERBB2_{369-377}$ peptide. ERBB2-specific T-cells displayed high peptide-specific IFN-γ production upon co-culture with antigen presenting cells (T2 cells) loaded with relevant ERBB2 peptide. As expected, no IFN-γ was produced upon exposure to T2 cells pulsed with irrelevant MART-$1_{26-35}$ peptide. As a positive control for functionality, MART-1 specific T-cells recognized and reacted against MART-$1_{26-35}$ peptide-loaded T2 cells (FIG. 2A).

The functional avidity of these T-cells were further evaluated by analyzing the production of IFN-γ in response to incubation with T2 target T-cells pulsed with titered amounts of $ERBB2_{369-377}$ peptide. $ERBB2_{369-377}$-specific T-cells exerted high functional avidity, as they were capable of secreting high amounts of IFN-γ even at low concentrations (1 nM) of specific peptide (FIG. 2B). The ERBB2-specific T-cells ability to recognize endogenously processed $ERBB2_{369-377}$ peptide was therefore investigated. Co-culture assays were performed utilizing ERBB2-specific T-cells with HLA-A2 matched or mismatched ovarian, breast, and melanoma cancer cells that express different levels of ERBB2 protein (Lanitis et al., PLoS ONE 7, e49829, 2012). $ERBB2_{369-377}$-specific CD8+ T-cells specifically recognized and secreted IFN-γ upon interaction with ERBB2+ HLA-A2+ ovarian or breast cancer cells, while no recognition of HLA-A2- or ERBB2-tumors was observed (FIG. 2C) There was no correlation between the intensity of ERBB2 surface expression by tumor cell lines and the IFN-γ secretion by T-cells. To this end, the expression of various components of antigen processing machinery (APM) by tumor cells was investigated, including TAP1, TAP2, tapasin and LMP2 via real time PCR (RT-PCR) to determine if deficiencies existed in the peptide-processing pathway of these tumor cells. ERBB2+ tumor cell lines that were recognized to a lesser extent by the $ERBB2_{369-377}$-specific T-cells (SKOV-3 and OVCAR-3) (FIG. 2C) displayed a reduced mRNA expression of tested APM molecules (FIG. 2D). Tumor cell lines that were well recognized by the $ERBB2_{369-377}$-specific T-cells (OVCAR-2, OV55-2 and MDA231) (FIG. 2C) displayed a higher level of expression in most of the APM molecules investigated (FIG. 2D). Therefore, lack of recognition of some ovarian tumors by $ERBB2_{369-377}$-specific T-cells may be attributed, in part, to a lack of necessary APM components in the tumor cells, as observed elsewhere (Han et al., Clin Cancer Res 14, 3372-3379, 2008). This observation highlights that both ERBB2 and HLA-A2 molecules are required, but not sufficient, for optimal immune recognition. Together, it can be concluded that vaccine-primed $ERBB2_{369-377}$-specific T-cells exert potent effector functions against peptide-loaded targets and HLA-A2 matched ERBB2-expressing tumor cells.

Example 3: Identification and Isolation of ERBB2-Specific TCR α/β Genes

Tumor recognition by T-cells is often accompanied with specific upregulation of T-cell activation surface antigens such as the early activation marker, CD69. In order to capture $ERBB2_{369-377}$-specific T-cells with high avidity for tumor-presented $ERBB2_{369-377}$ peptide, the ERBB2-specific T-cells were co-cultured with HLA-A2$^+$ ERBB2$^+$ MDA231 cells for 24 hours. ERBB2-specific T-cells that up-regulated CD69 (FIG. 7) and bound HLA-A2/$ERBB2_{366-377}$ tetramer were then isolated via fluorescence-activated flow sorting (FACS). In order to determine the TCR variable (TCRV) α-chain and TCRVβ-chain repertoire of the captured ERBB2-specific T-cells, total RNA was isolated from the sorted cells and subjected to 5' RACE. Twenty-three individual α-chain cDNA clones and fourteen individual β-chain cDNA clones were fully sequenced from two independent PCR reactions. Sequence data demonstrated two relatively dominant sequences in the TCRV(3 repertoire that belonged to the BV3-1(9S1) family of β-chains. More heterogeneity was observed in the TCRVα repertoire, with two repeats each for the AV3 and the AV12-1 α-chains (Table 1).

TABLE 1

TCR α and β DNA Constructs

TCR α and β chain sequencing results

| TRAV | Number of Clones | TRAVB | Number of Clones |
|---|---|---|---|
| AV1-1 | 1 | BV2 (22s1) | 1 |
| AV1-2 | 1 | BV3-1 (9S1) | 2, 3 |
| AV2 | 1 | BV4-1 (7S1) | 1 |
| AV3 | 2 | BV4-3 (7S2) | 1 |
| AV10 | 1 | BV5-1 (5S1) | 1 |
| AV12-1 | 2, 1 | BV5-4 (5S6) | 1 |
| AV12-2 | 1, 1, 1, 1 | BV5-6 (5S2) | 1 |
| AV17 | 1 | BV20-1 (2S1) | 1, 1, 1 |
| AV21 | 1, 1 | | |
| AV38-1 | 1 | | |
| AV38-2 | 1, 1, 1, 1, 1, 1 | | |

TCR α/β retroviral constructs

| Constuct Number | TCR Construct |
|---|---|
| 1 | AV12-1 BV3-1 (CB-1) |
| 2 | AV3 BV3-1 (CB-1) |
| 3 | AV12-2a BV3-1 (CB-1) |
| 4 | AV12-2b BV3-1 (CB-1) |
| 5 | AV12-2a BV3-1 (CB-2) |
| 6 | AV12-2b BV3-1 (CB-2) |
| 7 | AV3 BV3-1 (CB-2) |
| 8 | AV12-1 BV3-1 (CB-2) |

TCR α and β chains that presented more than once in the TCR repertoire were subcloned into the MSGV-1 retroviral backbone. A total of eight retroviral vectors harboring the α- and β-chain cDNAs were constructed (Table 1). Retroviruses encoding the eight different TCR α/β combinations were produced and utilized for the transduction of SupT1 cells. Subsequently, the genetically-modified SupT1 cells were stained with HLA-A2/$ERBB2_{369-377}$ tetramer and assessed via flow cytometry to identify TCRs with specificity for the $ERBB2_{369-377}$ peptide. One out of eight (1/8) TCR combinations exhibited specific and strong binding to the HLA-A2/$ERBB2_{369-377}$ tetramer (FIG. 3A). Hence, this paired TCR harboring the AV3 α-chain (SEQ ID NOs: 1 and 2) and the BV3-1 β-chain (SEQ ID NOs: 3 and 4) was chosen for further characterization (herein referred to as HLA-A2/ERBB2 TCR7, SEQ ID NOs: 5, 6 and 7).

Figure 3B:
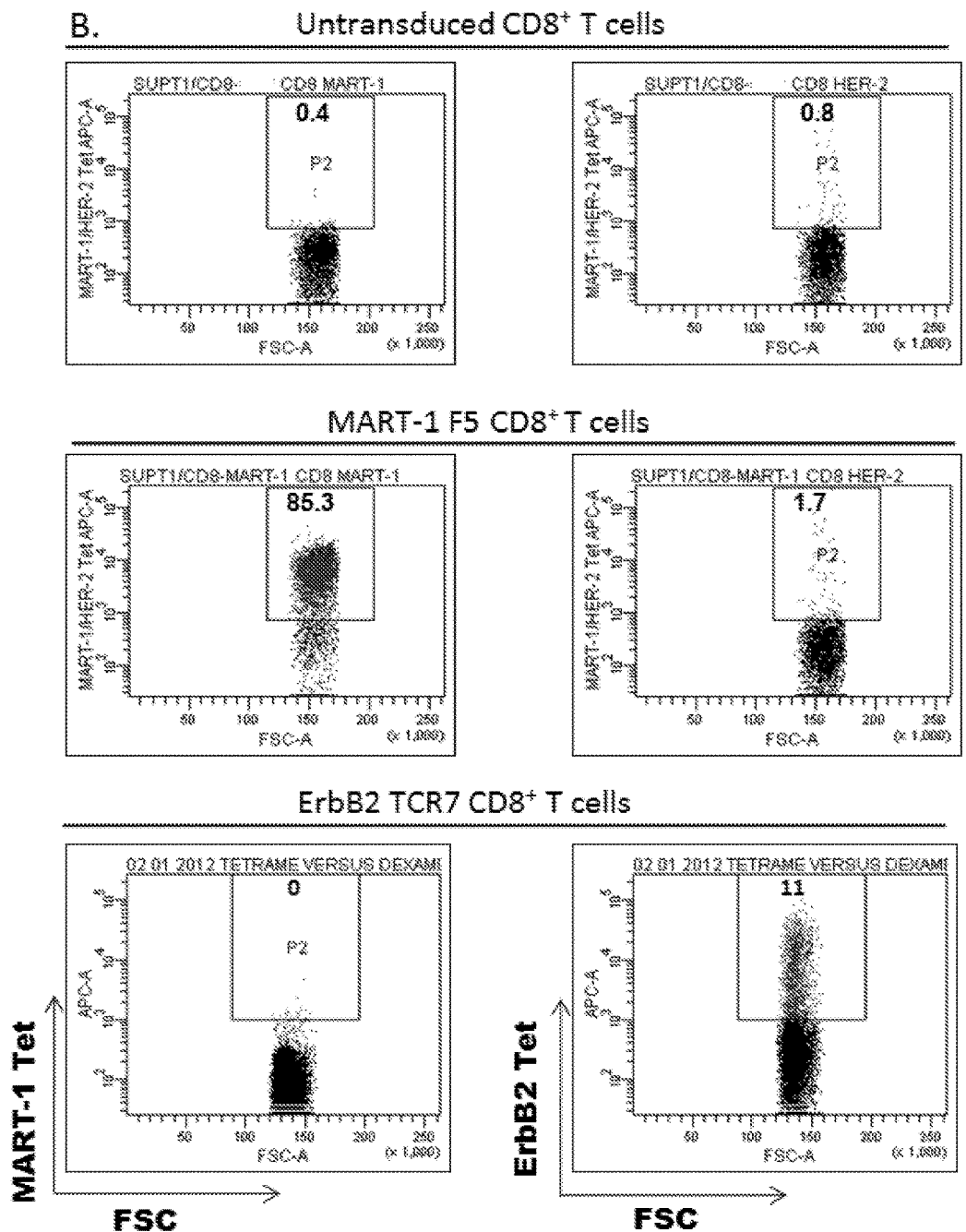
Figures 4A, 4B, 4C:
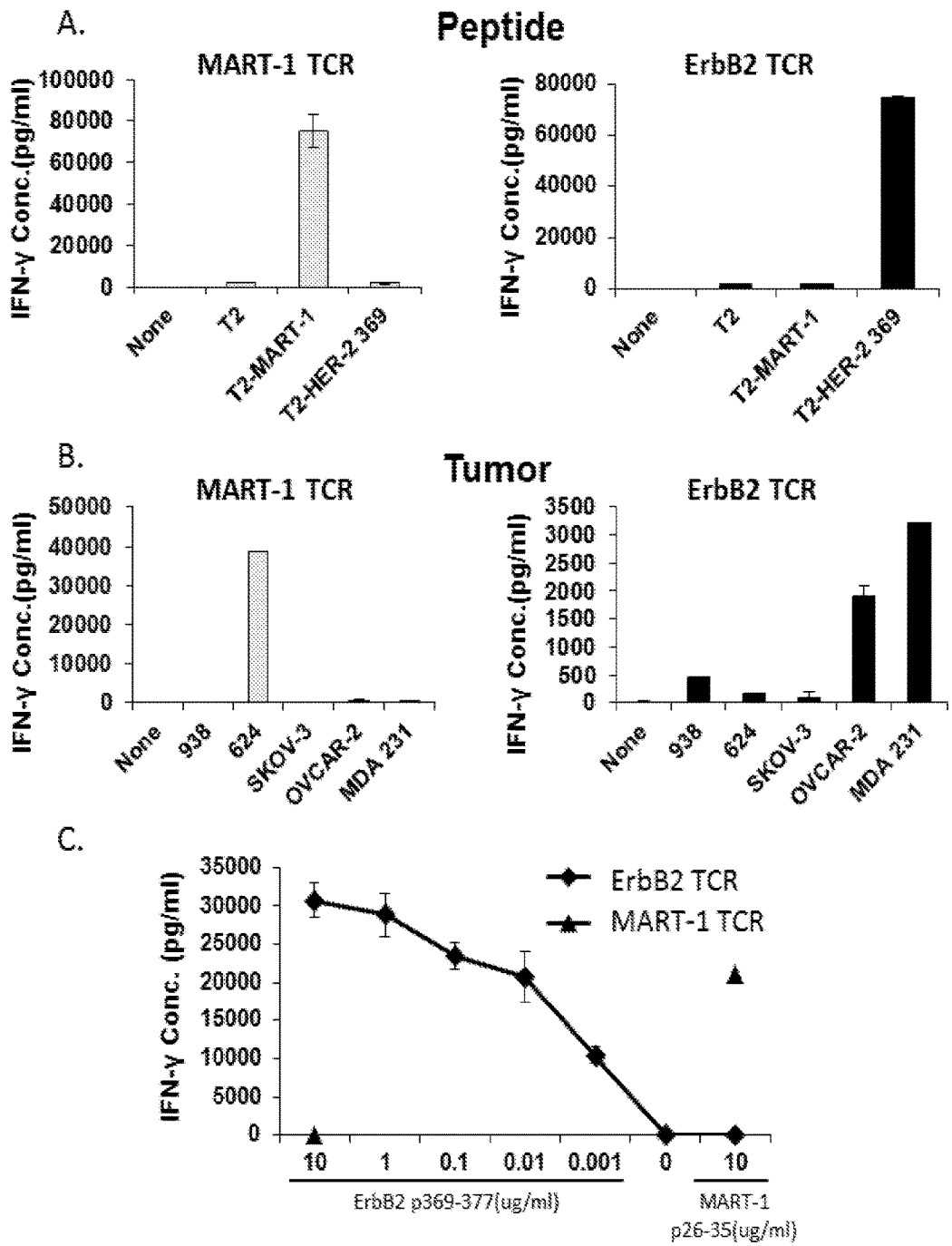
FIGS. 4A-4C are a series of histograms and graphs demonstrating that ERBB2$_{369-377}$-specific T-cells show potent IFN-γ production in response to ERBB2-peptide loaded targets and ERBB2-expressing cancer cell lines in vitro.

Example 4: Retroviral Transfer of $ERBB2_{369-377}$-specific TCR7 into CD8$^+$ T-cells Confers Antigen Specificity Next, the functional properties that TCR7 (SEQ ID NOs: 5, 6 and 7) confers upon expression in primary human T-cells was investigated. Retroviral TCR gene transfer into CD8$^+$ T-cells resulted in specific HLA-A2/$ERBB2_{369-377}$ tetramer binding (FIG. 3B). However, the percentage of tetramer$^-$ cells was low (~10%) when compared to SupT1 cells, suggesting that transduced TCRs may not be assembled in a way that they can be detected or that mispairing with endogenous α-chains may have occurred. Importantly, even at low tetramer binding frequencies the ERBB2 TCR7 transduced T-cells demonstrated specific, robust reactivity against peptide-pulsed APC targets (FIG. 4A). ERBB2 TCR T-cells demonstrated high peptide avidity, as they secreted high IFN-γ levels at peptide concentrations as low as 1 ng/ml (FIG. 4C). Upon analyzing the tumor reactivity of the ERBB2 TCR CD8$^+$ T-cells, IFN-γ secretion was observed in response to HLA-A2$^+$ ERBB2$^+$ OVCAR-2 and MDA231 tumor cells at levels similar to that produced by the initial ERBB2 polyclonal T-cell population (FIG. 2C and FIG. 4B). No reactivity was observed against tumors lacking HLA-A2 or ERBB2 expression or HLA-A2$^+$ 624 melanoma cells expressing very low levels of ERBB2 (FIG. 4B).

Example 5: T-Cells Expressing $ERBB2_{369-377}$-Specific TCR7 Delay Tumor Growth in Vivo To determine the anti-tumor efficacy of T-cells expressing $ERBB2_{369-377}$-specific TCR7 in vivo, equal numbers of TCR7- or control MART-$1_{26-35}$ TCR-transduced CD8$^+$ T-cells and MDA231 tumor cells were subcutaneously co-injected into NOD/SCID/IL2-$\gamma_c^{null}$ (NSG) mice and monitored tumor outgrowth. MDA231 tumors grew aggressively with palpable tumors evident 14 days after injection. Compared to MART-1 TCR-specific T-cells, ERBB2 TCR7-transduced T-cells were capable of significantly delaying tumor burden over time (FIG. 5A). At the termination of the study, mice were euthanized and tumors were excised. Consistent with measured tumor volume (FIG. 5A), resected tumors from the ERBB2 TCR7 group were visibly smaller (FIG. 5B) and weighed significantly less compared to those in mice treated with the MART-1 TCR (FIG. 5C).

Example 6

Introduction of tumor-specific TCR genes has been proposed as a method to produce de novo antitumor lymphocytes for cancer immunotherapy without the need to isolate tumor-reactive T-cells (Cordaro et al., J Immunol 168, 651-660, 2002; Sadelain et al., Nat Rev Cancer 3, 35-45, 2003; Schumacher, Nat Rev Immunol 2, 512-519, 2002; Willemsen et al., Hum Immunol 64, 56-68, 2003). This proposition requires the existence of tumor antigens common to divergent human cancers and the isolation of a tumor-reactive TCR from the appropriate T-cell population that recognizes these natural tumor antigens. Since its discovery, the synthetic ERBB2$_{369-377}$ peptide has been widely investigated for the ex vivo and in vivo generation of ERBB2-specific CTLs following stimulation in vitro (Anderson et al., Clin Cancer Res 6, 4192-4200, 2000; Brossart et al., Cancer Res 58, 732-736, 1998; Keogh et al., J Immunol 167, 787-796, 2001; Liu et al., Cancer Res 64, 4980-4986, 2004; Rongcun et al., J Immunol 163, 1037-1044, 1999; Seliger et al., Int J Cancer 87, 349-359, 2000; zum Buschenfelde et al., Cancer Res 62, 2244-2247, 2002) or vaccination (Brossart et al., 2000; Knutson et al., 2002; Murray et al., 2002; Peoples et al., J Clin Oncol 23, 7536-7545, 2005; Zaks and Rosenberg, Cancer Res 58, 4902-4908, 1998). Although some ERBB2-specific T-cells exert high reactivity against ERBB2-peptide, but fail to recognize endogenously processed peptide presented by ERBB2+ tumors (Conrad et al., J Immunol 180, 8135-8145, 2008; Zaks and Rosenberg, Cancer Res 58, 4902-4908, 1998), recent work demonstrates that ERBB2$_{369-377}$-specific T cells cross react with overlapping HLA Class I-restricted ERBB2$_{373-382}$ peptide (Henle et al., J Immunol 190, 479-488, 2013). Importantly, ERBB2$_{373-382}$ is naturally processed and ERBB2$_{373-382}$-specific T cells also cross react with ERBB2$_{369-377}$ peptide (Henle et al., J Immunol 190, 479-488, 2013), suggesting continued clinical importance for ERBB$^2_{369-377}$ peptide though controversy of its natural processing exists.

The present invention includes isolating and testing ERBB2-reactive T-cells from HLA-A2+ patients with ERBB2+ breast tumors that had been vaccinated with autologous preconditioned dendritic cells (DC1) pulsed with ERBB2 HLA class I and II peptides (Czerniecki et al., Cancer Res 67, 1842-1852, 2007). Dendritic cells polarized toward the DC1 phenotype produce cytokines and chemokines critical for maximizing antitumor immunity (Xu et al., J Immunol 171, 2251-2261, 2003) and therefore may enhance the efficacy of antitumor vaccines and offer a strong approach to induce and expand tumor-reactive T-cells in vivo and ex vivo. After one round of ex vivo stimulation with DC1 cells loaded with ERBB2$_{369-377}$ peptide, the frequency of ERBB2$_{369-377}$ peptide-specific T-cells increased to a level (~3.4%) sufficient for robust downstream functional analysis. Of note, these T-cells were capable of recognizing peptide loaded onto T2 cells at nM levels, but also HLA-A2+ ERBB2-expressing tumors. Fluorescence-activated cell sorting allowed to maximize the purity of ERBB2-specific T-cells (~95%), and molecular analysis of the TCR repertoire and subsequent testing of various TCR α and β combinations led to identify and isolate herein a novel ERBB2$_{369-377}$-specific TCR (TCR7 AV3/BV3-1) (SEQ ID NOs: 1-7).

Retroviral particles encoding the ERBB2 TCR were propagated and utilized for the genetic engineering of primary T-cells. Nearly a 10% TCR expression efficiency by transduced T-cells was observed, as measured by binding to ERBB2$_{369-377}$ multimers. Although the percentage of multimer+cells was low in primary human T-cells, high expression of ERBB2 TCR in SupT1 cells (~80%) that lack endogenous TCR α and β chains was observed, suggesting the possibility that mispairing with endogenous TCR α/β-chains impairs proper paired assembly of the exogenous TCR chains on the surface of the transduced T-cells. Nevertheless transduced T-cells demonstrated HLA-A2-restricted, ERBB2-specific effector T-cells functions, as measured by cytokine release against peptide-pulsed targets and HLA-A2+ ERBB2+ ovarian and breast cancer tumor cells lines. Similar to the starting ERBB2-specific T-cell population, high functional avidity of the ERBB$^2_{369-377}$ TCR transduced T-cells was demonstrated by their ability to recognize T2 cells pulsed with very low amounts of the cognate peptide (ing/nil) and their ability to significantly delay tumor outgrowth in a human breast cancer xenograft model.

Further preclinical refinement of this TCR gene approach is warranted in order to lessen chimeric dimer formation and increase the expression of the exogenous TCR on the T-cell surface. This can be achieved by replacing the constant region of the human TCR chains by their murine counterparts (Cohen et al., Cancer Res 66, 8878-8886, 2006), the introduction of additional cysteine residues within the constant region of the TCR α and β chains (Cohen et al., Cancer Res 67, 3898-3903, 2007; Voss et al., J Immunol 180, 391-401, 2008), the provision of exogenous CD3 molecules (Ahmadi et al., Blood 118, 3528-3537, 2011), and/or the inclusion of small interfering RNA (siRNA) to specifically down-regulate the endogenous TCR (Okamoto et al., Clin Cancer Res 8, 3407-3418, 2009). Alternatively, the reactivity of ERBB2 TCR T-cells can be potentiated by immune checkpoint blockade via the co-administration of recombinant human antibodies specific for negative immunoregulatory molecules, such as B7-H4, which is often expressed by tumor cells (Dangaj et al., Cancer research, 2013).

In summary, the ERBB2$_{369-377}$-specific TCR of the present invention represents a readily available composition that can be utilized to generate autologous tumor antigen-specific T-cells without the need to identify antitumor T-cells unique for each patient. This invention redirects normal T-cell specificity by TCR gene transfer and can yield sufficient numbers of T-cells with high avidity and specificity for the ERBB2$_{369-377}$ peptide for the treatment of a variety of common epithelial or other ERBB2-expressing malignancies. Thus the compositions and methods of this invention provide great potential applications in the adoptive immunotherapy field.

The disclosures of each and every patent, patent application, and publication cited herein are hereby incorporated herein by reference in their entirety.

While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed is:

1. A method of inhibiting the growth of tyrosine-protein kinase HER2/Neu (ERBB2)-expressing tumor cells in a human in need thereof, the method comprising administering to the human a therapeutically effective amount of a T cell transduced with a recombinant polynucleotide encoding a T cell receptor (TCR), wherein the recombinant polynucleotide encodes a TCR alpha chain having the sequence of SEQ ID NO: 2 or 6 and a TCR beta chain having the sequence of SEQ ID NO: 4 or 7, wherein the recombinant polynucleotide expresses a functional ERBB2-specific TCR reactive with an HLA-A2+ restricted ERBB2 epitope, and wherein the growth of the ERBB2-expressing tumor cells is inhibited.

2. The method of claim 1, wherein the cancer is a cancer of the breast, ovary, stomach, kidney, colon, bladder, salivary gland, endometrium, pancreas or lung.

3. The method of claim 1, wherein the modified cell is a CD8+ T cell.

4. The method of claim 1, wherein the modified cell is autologous with respect to the human undergoing treatment.

5. A method of inhibiting the growth of tyrosine-protein kinase HER2/Neu (ERBB2)-expressing tumor cells in a human in need thereof, the method comprising administering to the human a therapeutically effective amount of a T cell transduced with a recombinant polynucleotide encoding a T cell receptor (TCR), wherein the recombinant polynucleotide encodes a TCR alpha chain having the sequence of SEQ ID NO: 2 and a TCR beta chain having the sequence of SEQ ID NO: 4, wherein the recombinant polynucleotide expresses a functional ERBB2-specific TCR reactive with an HLA-A2+ restricted ERBB2 epitope, and wherein the growth of the ERBB2-expressing tumor cells is inhibited.

6. The method of claim 5, wherein the cancer is a cancer of the breast, ovary, stomach, kidney, colon, bladder, salivary gland, endometrium, pancreas or lung.

7. The method of claim 5, wherein the modified cell is a CD8+ T cell.

8. The method of claim 5, wherein the modified cell is autologous with respect to the human undergoing treatment.

* * * * *